US008272875B1

(12) United States Patent
Jurmain

(10) Patent No.: US 8,272,875 B1
(45) Date of Patent: Sep. 25, 2012

(54) EDUCATIONAL DEVICE FOR SIMULATING ADDICTIVE BEHAVIOR AND METHOD OF USING

(75) Inventor: Richard N. Jurmain, Eau Claire, WI (US)

(73) Assignee: Realityworks, Inc., Eau Claire, WI (US)

( * ) Notice: Subject to any disclaimer, the term of this patent is extended or adjusted under 35 U.S.C. 154(b) by 0 days.

(21) Appl. No.: 09/417,227

(22) Filed: Oct. 13, 1999

Related U.S. Application Data

(63) Continuation-in-part of application No. 09/264,762, filed on Mar. 9, 1999, now abandoned.

(51) Int. Cl.
*G09B 19/00* (2006.01)

(52) U.S. Cl. .......................................... 434/236; 434/238

(58) Field of Classification Search .................. 131/270; 434/262, 238, 236; 600/72
See application file for complete search history.

(56) References Cited

U.S. PATENT DOCUMENTS

| | | | | |
|---|---|---|---|---|
| 3,889,163 A | * | 6/1975 | Symmes | 361/232 |
| 3,999,412 A | | 12/1976 | Boroski et al. | 70/269 |
| 4,037,719 A | | 7/1977 | Perlmutter | 206/266 |
| 4,076,118 A | | 2/1978 | Karlsson | 206/268 |
| 4,138,722 A | | 2/1979 | Bonnett | 364/415 |
| 4,223,801 A | | 9/1980 | Carlson | 221/3 |
| 4,293,845 A | | 10/1981 | Villa-Real | 340/309.3 |
| 4,311,448 A | | 1/1982 | Strauss | 431/14 |
| 4,853,854 A | * | 8/1989 | Behar et al. | 700/295 |
| 4,862,431 A | | 8/1989 | Drouin | 368/10 |
| 4,966,164 A | * | 10/1990 | Colsen et al. | 607/72 |
| 4,984,158 A | | 1/1991 | Hillsman | 364/413.04 |
| 5,203,472 A | * | 4/1993 | Levenbaum et al. | 221/15 |
| 5,217,379 A | | 6/1993 | Kirschenbaum et al. | 434/236 |
| 5,228,848 A | | 7/1993 | Kim | 431/253 |
| 5,285,430 A | | 2/1994 | Decker | 368/281 |
| 5,554,967 A | | 9/1996 | Cook et al. | 340/390.15 |
| 5,673,691 A | | 10/1997 | Abrams et al. | 128/630 |
| 5,778,897 A | * | 7/1998 | Nordlicht | 131/270 |
| 5,813,863 A | * | 9/1998 | Sloane et al. | 434/236 |
| 5,871,398 A | | 2/1999 | Schneier et al. | 463/16 |
| 5,893,371 A | * | 4/1999 | Rose et al. | 131/270 |
| 5,908,301 A | | 6/1999 | Lutz | 434/236 |
| 5,913,310 A | | 6/1999 | Brown | |
| 5,918,603 A | | 7/1999 | Brown | 128/897 |
| 6,125,082 A | * | 9/2000 | Reid | 368/10 |

(Continued)

FOREIGN PATENT DOCUMENTS

WO    WO 02/19178    3/2002

OTHER PUBLICATIONS

"Stop Smoking with the Medically Proven Life Sign System" package and instructions, 1996.

(Continued)

*Primary Examiner* — Robert J Utama
(74) *Attorney, Agent, or Firm* — Sherrill Law Offices, PLLC

(57) ABSTRACT

An addiction simulator for use in an educational program, operable for (i) periodically requesting simulated addictive behavior, (ii) receiving a satisfaction signal from an assigned individual in response to a generated request, representing consumption of an amount of addictant in limited supply, and (iii) refusing acceptance of a satisfaction signal when the supply of addictant has been exhausted. The duration of the interval between requests can based upon a physiological characteristic of the assigned individual.

98 Claims, 17 Drawing Sheets

U.S. PATENT DOCUMENTS

| | | | |
|---|---|---|---|
| 6,247,643 B1 | 6/2001 | Lucero | 235/380 |
| 6,368,111 B2 * | 4/2002 | Legarda | 434/236 |

OTHER PUBLICATIONS

"Life Sign Program Guide," May 1998.

"LifeSign" Help Cards, May 1998.

"LifeSign" Lesson Plan, Aug. 1998.

"LifeSign, The Better, Faster, Cheaper way to Quit Smoking" web site information, May 1999.

"Cigarette packets to tell you to quit?" www.msnbc.com/news, Mar. 13, 2001.

* cited by examiner

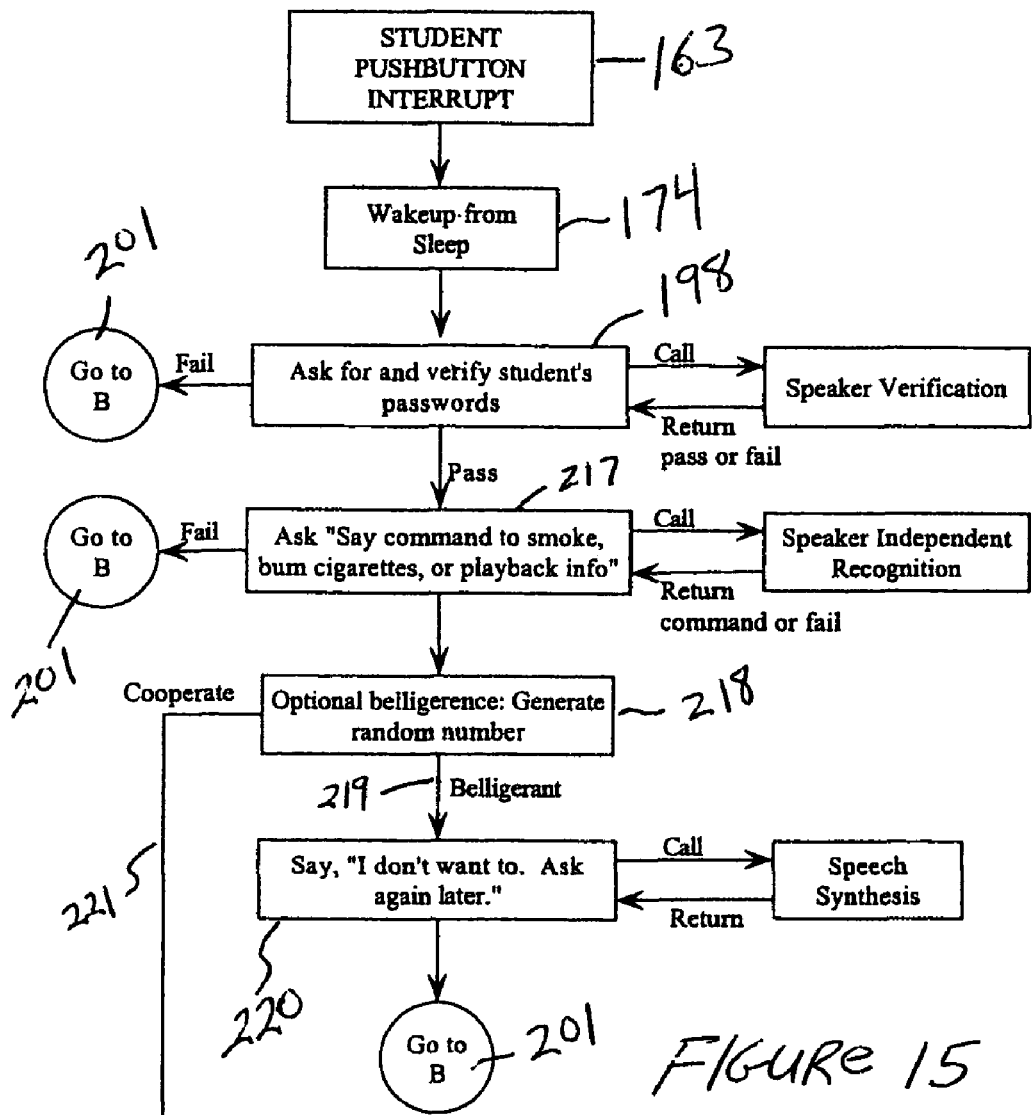
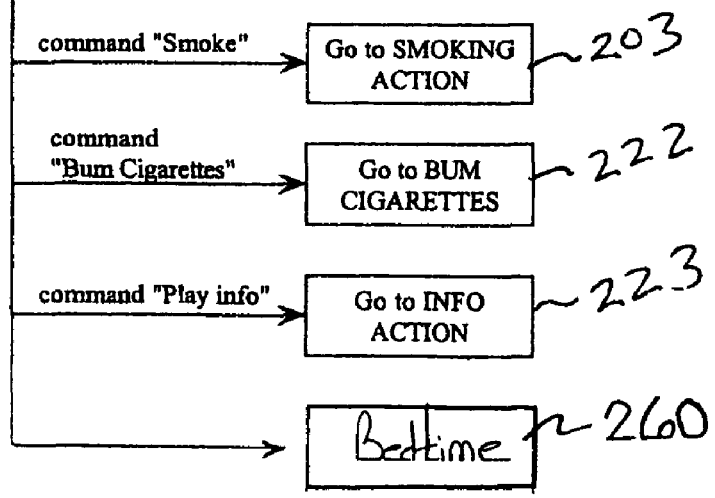
FIGURE 15

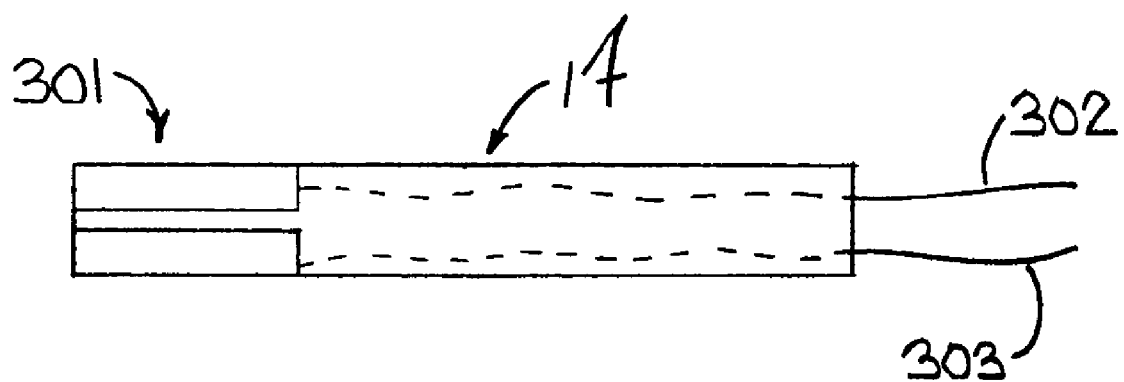

EDUCATIONAL DEVICE FOR SIMULATING ADDICTIVE BEHAVIOR AND METHOD OF USING

This application is a continuation-in-part of U.S. patent application Ser. No. 09/264,762 filed 9 Mar. 1999 now abandoned.

FIELD OF THE INVENTION

The present invention relates generally to the field of smoking simulators, and more particularly to the field of devices which demonstrate to teenagers the loss of control over their lives caused by the habit of smoking cigarettes.

DESCRIPTION OF RELATED TECHNOLOGY

Cigarette smoking is an addictive habit which is extremely difficult to break. The harm to a person's health caused by smoking is well documented. Furthermore, the habit is costly to support even if the user is not a heavy smoker. Numerous devices have been developed to help smokers quit, such as U.S. Pat. No. 3,999,412, issued to Boroski et al. The Boroski et al. device is a cigarette case which counts and rations the number of cigarettes dispensed to the user.

Various smoking elimination systems utilize a timer which establishes a basic timing period during which a cigarette case or lighter is locked. These patents include U.S. Pat. No. 3,744,953, issued to Herr, U.S. Pat. No. 2,681,560, issued to Shuttleworth et al. and U.S. Pat. No. 2,643,527, issued to Harris. When the basic timing period is over, the cigarette lighter or box may be opened to permit a single use of a cigarette. Sometimes the timing period is manually adjustable and generally the timer must be manually reset each time a cigarette is removed from the case or a cigarette lighting operation takes place. In such a smoking elimination system, each time the user desires to smoke, she must try to operate the cigarette lighter or open the cigarette case to determine whether or not she can smoke. A related device is disclosed in U.S. Pat. No. 3,424,123, issued to Giffard, in which the lock is eliminated and a bell signals the user to that the basic timing period has expired.

Other more interactive programmable devices have been developed to assist, monitor, control or record various types of human behavior. U.S. Pat. No. 4,100,401, issued to Tutt et al. discloses a device that permits a user to input data representing caloric intake as well as expected caloric expenditure rates. The device then displays the instantaneous net balance of unconsumed calories. The Tutt et al. device does not generate any personalized program for behavior modification or any personalized programmed schedule of future event times. U.S. Pat. No. 4,144,568, issued to Hiller et al. discloses a device which records various personalized data and provides related output data to the user. While the output data may be of interest to the user and might conceivably affect the user's future activities, the Hiller et al. device does not actually stimulate human behavior modification in any meaningful sense.

U.S. Pat. No. 4,281,389, issued to Smith describes a device which is programmed to provide personalized metronome like audible signals designed to pace every other stride of a long distance runner. The necessary data may be manually input prior to the run, or the runner may manipulate manually accessible controls and modify the programming so as to conform with her actual stride frequency during a given run. Thereafter, the device is capable of providing a modified programmed stride rate so as to signal the stride rate required to achieve a desired run time.

U.S. Pat. No. 4,360,125, issued to Martindale et al. shows a medicine dispenser which signals the user each time a medication event is supposed to occur and also records the time at which each medication access by the user actually occurs. The device only provides a health care worker with such a factual record and no attempt is made to create any modified program schedule for the future. U.S. Pat. No. 4,428,050, issued to Pellegrini et al. discloses a device which accepts personalized data relating to skin tanning parameters and then provides the user with a program which should be followed so as to achieve a desired degree of tanning. There is no baseline learning phase, nor is the device directed toward modification of habitual human behavior associated with a sequence of events.

U.S. Pat. No. 4,853,854, issued to Behar et al., discloses a behavior modification device to help a user quit smoking. The device is a small pocket sized device that is controlled by a microprocessor programmed in read only memory with a specific control program. When a user activates the device by means of an external switch, the device begins a baseline establishment phase of the behavior modification process. Each time the user performs a habit related event, the user informs the device through the use of a switch. The device records the event at the time of its occurrence for future processing. The device remains in the baseline phase for a predetermined period of time. When the baseline period ends, the device notifies the user and proceeds to the withdrawal phase of the program. Once the personalized withdrawal phase occurs, the device prompts the user by providing visual and audio stimuli as to when the user may smoke one cigarette. A visual display also informs the user as to when permission to smoke again will be granted. The user notifies the device that the prescribed event has been committed by activating a switch.

Some devices exist which require a user to actually exhale into a handheld unit. An example of such a device is disclosed in U.S. Pat. No. 5,291,898, issued to Wolf. The Wolf device is a breath analyzer which contains a tube into which a user exhales, the breath sample being analyzed for its alcohol content.

While some of the aforementioned devices deal with smoking and behavior modification, none address the problem of preventing a person from smoking who has never engaged in the habit. Further, none of these devices are actuated in a manner that attempts to accurately simulate the actual act of smoking. For example, none of the prior art devices simulate the spending of money to purchase cigarettes, cause the user to crave a cigarette at inconvenient times due to nicotine addiction or simulate coughing caused by long term cigarette use.

SUMMARY OF THE INVENTION

The present invention is a device which demonstrates to prospective smokers, who are most likely teenagers, the loss of control over their lives caused by smoking. The device is preferably a box which has the same dimensions and appearance as a package of cigarettes. The box contains a microprocessor connected to a liquid crystal display which displays messages to the user, or preferably a voice recognition and synthesis circuit to permit spoken interaction with the device. The device gives orders to the user which simulate the effects of smoking while monitoring the user's responses. The device also presents the user with general information relating to the disadvantages of smoking and emphasizes the control that the habit of smoking can exert on the user's life.

The simulator also includes a vibrator and speaker or beeper to prompt the user to read the LCD display. A bellows switch is included to detect the action of the user inhaling or exhaling through a tube to simulate the drawing in of air through a cigarette and the need to catch one's breath after each draw. The tube is replaceable to permit the use of the simulator by different users. Occasionally the device will cough or the user will be prompted by the device to cough and the act of coughing is detected by a built in microphone.

In order to simulate the expense associated with the habit of smoking, a slot can be formed in the side of the simulator box which is sufficiently large to accept a dollar bill or suitable money substitute. A microswitch is placed within the cavity to detect when a dollar bill is actually inserted into the simulator. In a classroom environment, the currency accepting cavity can be opened by a key which is in the possession of the teacher. The times when the student is both permitted to smoke or required to smoke can be programmed into or calculated by the unit, and a pushbutton on the outside of the device can toggle through a choice of such time periods in, for example, five minute increments.

In one preferred embodiment of the device, the smoking simulation program which can be experienced by use of the device will last approximately three days. The first day simulates the demands of smoking approximately one half of a package per day. The second day simulates about one pack per day. The third day of the simulation approximates the use of two packs per day. The messages displayed by the device, which can include both requests and information, become increasingly demanding and onerous as the simulation progresses. Ideally, the simulator is capable of delivering hundreds of such messages in order to maintain the user's interest. When the program is complete, the student has gained a better understanding of the expense and inconvenience of smoking. The device is capable of storing various parameters related to the student's interaction with the device, and these parameters can be reviewed by the teacher in order to evaluate the level of the student's performance.

BRIEF DESCRIPTION OF THE DRAWINGS

FIG. 15 is a flowchart depicting the STUDENT PUSH-BUTTON INTERRUPT subroutine associated with the present invention.

FIG. 19 is a side view of a second aspect of a simulated cigarette associated with the present invention.

DETAILED DESCRIPTION OF THE PREFERRED EMBODIMENTS

Nomenclature

Figure 3:
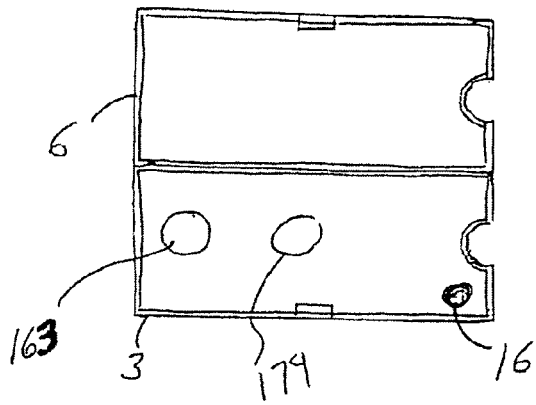
FIG. 3 is a plan view of the apparatus depicted in FIG. 1.
Figure 1:
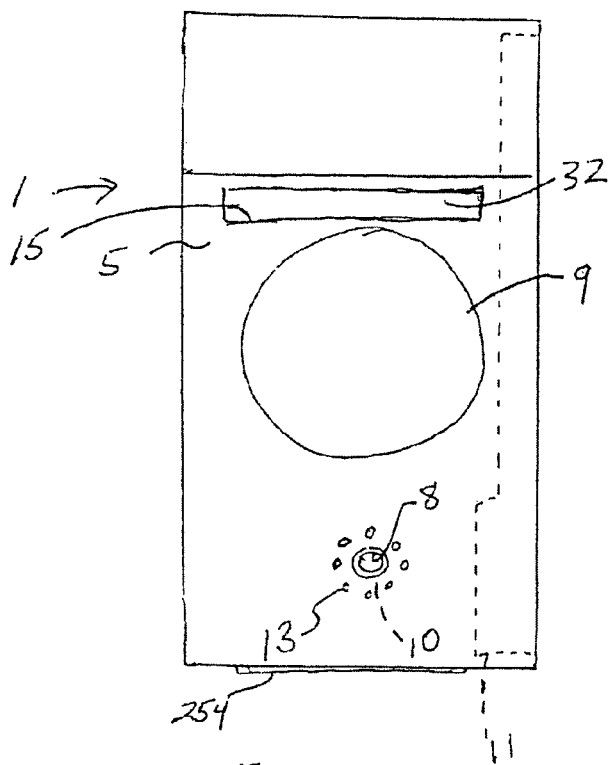
FIG. 1 is a front elevation of a smoking simulator constructed according to the principles of the present invention.
Figure 2:
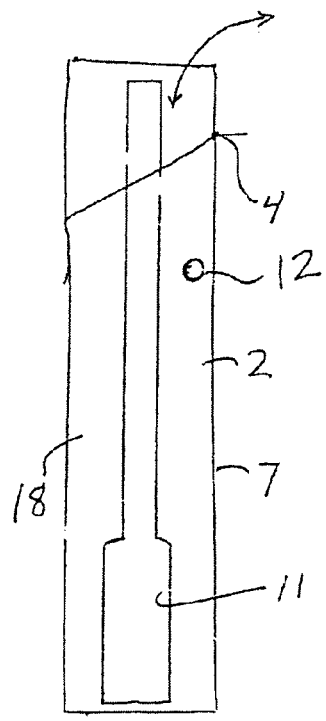
FIG. 2 is a side elevation of the apparatus depicted in FIG. 1.

| | |
|---|---|
| 1 | Smoking Simulation Apparatus, Simulator or Device |
| 2 | Case or Enclosure |
| 3 | Edge |
| 4 | Hinge |
| 5 | Front Surface |
| 6 | Top |
| 7 | Rear Surface |
| 8 | Receptacle |
| 9 | Speaker |
| 10 | Microphone |
| 11 | Recess (Storage Area) |
| 12 | Switch |
| 13 | Peripheral Holes or Perforations |
| 15 | Display Window |
| 16 | Earphone Jack |
| 17 | Puffing Device (Simulated Cigarette) |
| 17s | Surface of Simulated Cigarette |
| 18 | Side |
| 19 | Microcontroller, Microprocessor or Integrated Circuit |
| 20 | Random Access Memory Chip |
| 21 | Dataport D7 |
| 22 | Dataport D6 |
| 23 | Dataport D5 |
| 24 | Dataport D4 |
| 25 | Dataport D3 |
| 26 | Dataport D2 |
| 27 | Dataport D1 |
| 30 | Dataport D0 |
| 32 | Visual Display |
| 33 | Core Ground |
| 34 | Core Power Supply Input |
| 35 | I/O port 1.7 |
| 36 | I/O port 1.6 |
| 37 | I/O port 1.5 |
| 38 | I/O port 1.4 |
| 39 | I/O port 1.3 |
| 40 | I/O port 1.2 |
| 41 | I/O port 1.1 |
| 42 | I/O port 1.0 |
| 43 | I/O port 0.7 |
| 44 | I/O port 0.6 |
| 45 | I/O port 0.5 |
| 46 | I/O port 0.4 |
| 47 | I/O port 0.3 |
| 48 | I/O port 0.2 |
| 49 | I/O port 0.1 |
| 50 | I/O port 0.0 |
| 51 | Memory Data Port D0 |
| 52 | Memory Data Port D1 |
| 53 | Memory Data Port D2 |

| | |
|---|---|
| 54 | Memory Data Port D3 |
| 55 | Memory Data Port D4 |
| 56 | Memory Data Port D5 |
| 57 | Memory Data Port D6 |
| 58 | Memory Data Port D7 |
| 59 | Data Bus |
| 60 | Address Bus |
| 61 | Address port A1 |
| 62 | Address port A2 |
| 63 | Address port A3 |
| 64 | Address port A4 |
| 65 | Address port A6 |
| 66 | Address port A7 |
| 67 | Address port A8 |
| 68 | Address port A9 |
| 69 | Address port A10 |
| 70 | Address port A11 |
| 71 | Address port A12 |
| 72 | Address port A5 |
| 73 | Address port A13 |
| 74 | Address port A14 |
| 75 | Address port A15 |
| 76 | Address port A0 |
| 77 | Power Supply |
| 78 | Analog Power Supply |
| 79 | Battery |
| 80 | Capacitor |
| 81 | Diode |
| 82 | Air Jets |
| 83 | Resistor |
| 84 | 470 Microfarad Capacitor |
| 85 | Audio Preamplifier |
| 86 | Terminal |
| 87 | Core Power Supply |
| 88 | 2.2 Ohm Resistor |
| 89 | Electrolytic Capacitor |
| 90 | Input/Output Power Source |
| 91 | Resistor |
| 92 | Capacitor |
| 93 | Resistor |
| 94 | Capacitor |
| 95 | Reset Terminal |
| 96 | Diode |
| 97 | Bandpass Filter and Amplifier |
| 98 | Automatic Gain Control Circuit (AGC) |
| 99 | IGAIN0 Terminal |
| 100 | IGAIN1 Terminal |
| 101 | 1000 Ohm Resistor |
| 102 | 22000 Ohm Resistor |
| 103 | 10000 Ohm Resistor |
| 104 | First Stage Amplifier |
| 105 | Third Stage Amplifier |
| 106 | 0.22 Picofarad Capacitor |
| 107 | 4700 Ohm Resistor |
| 108 | 680000 Ohm Resistor |
| 109 | 27000 Ohm Resistor |
| 110 | 1000 Ohm Resistor |
| 111 | 0.22 Picofarad Capacitor |
| 112 | Fourth Stage Amplifier |
| 113 | 56000 Ohm Resistor |
| 114 | 1000 Ohm Resistor |
| 115 | Low Analog Output Terminal |
| 116 | High Analog Output Terminal |
| 117 | Digital Ground |
| 118 | Digital Power Supply Input |
| 119 | Digital Ground |
| 120 | Digital Power Supply Input |
| 121 | 0.1 Microfarad Capacitor |
| 122 | Digital Ground |
| 123 | Core Ground Input |
| 124 | Core Power Supply Input |
| 125 | 0.1 Microfarad Capacitor |
| 126 | 0.1 Microfarad capacitor |
| 127 | Core Ground |
| 128 | Core Ground |
| 130 | Analog Ground Input |
| 131 | Analog Power Input |
| 132 | 0.1 Microfarad Capacitor |
| 133 | Analog Ground Connection |
| 134 | 14.3 MegaHertz Crystal |
| 136 | Picofarad Capacitor |
| 137 | 27 Picofarad Capacitor |
| 138 | Oscillator 1 Output |
| 139 | Oscillator 1 Input |
| 140 | 32.768 KiloHertz Crystal |
| 141 | 27 Picofarad Capacitor |
| 142 | 27 Picofarad Capacitor |
| 143 | Oscillator 2 Input |
| 144 | Oscillator 2 Output |
| 145 | Read Code port |
| 146 | Write Code port |
| 148 | Read Data port |
| 149 | Write Data port |
| 150 | 74HCT08 Integrated Circuit |
| 151 | Chip Enable port |
| 152 | Output Enable port |
| 153 | Write Enable port |
| 154 | Pulse Width Modulation Output |
| 155 | Pulse Width Modulation Output |
| 160 | Microswitch |
| 161 | Bellows Switch |
| 162 | Sound Activated Switch |
| 163 | Pushbutton (Student) |
| 164 | Flow Restriction Portion |
| 165 | Straw Portion |
| 166 | Mounting Bracket |
| 167 | Check Valve |
| 168 | Filter |
| 169 | Overview Flowchart |
| 170 | POWERUP AND INITIALIZE |
| 171 | RUN |
| 172 | Bootup Procedure |
| 173 | Password Request and Store |
| 174 | SLEEP Mode |
| 175 | Voice Verification |
| 176 | Time Entry Prompt |
| 177 | Clock Startup |
| 178 | Teacher Prompt |
| 179 | Pushbutton (Teacher) |
| 180 | Teacher Interrupt |
| 181 | Wakeup from Sleep |
| 182 | Request Prompt |
| 183 | Report Command |
| 184 | Run Command |
| 185 | Buy Cigarettes Command |
| 186 | Packs per Day Command |
| 187 | Escalation Rate Command |
| 188 | Metabolic Rate Command |
| 189 | Susceptibility Command |
| 190 | Information Frequency Command |
| 191 | Set Number of Packages |
| 192 | Initial Smoking Rate |
| 193 | Escalation Rate |
| 194 | Metabolic Rate |
| 195 | Susceptibility |
| 196 | Information Rate |
| 197 | Return Path |
| 198 | Verification of Password |
| 199 | Brand Selection |
| 200 | Personality |
| 201 | Physiological Parameter Calculations |
| 202 | Nicotine Craving Level |
| 203 | SMOKING ACTION Module |
| 204 | Internal Timers |
| 205 | SMOKING NOTIFICATION Module |
| 206 | Notification Methods |
| 207 | Device Scheduler |
| 208 | INFORMATION NOTIFICATION Module |
| 209 | Notification Options |
| 210 | Notification Timer |
| 211 | COUGHING INTERRUPT Module |
| 212 | Notification Methods |
| 213 | Cough Prompt |
| 214 | Retry Option |
| 215 | Record Success |
| 216 | Record Failure |
| 217 | Student Command |
| 218 | Random Number Generator |
| 219 | Belligerence Path |
| 220 | Repetition Step |

-continued

| | |
|---|---|
| 221 | Cooperation Path |
| 222 | BORROWING or BUMMING Module |
| 223 | INFORMATION ACTION Module |
| 224 | Inventory Inquiry |
| 225 | None Available Announcement |
| 226 | Smoking Permitted Announcement |
| 227 | Continuous Listening Subroutine |
| 228 | Consumption Rate Calculator |
| 229 | Return Path |
| 230 | Counter |
| 231 | Demand |
| 232 | Message Bank |
| 233 | Message Generator |
| 234 | Sound Monitor |
| 235 | Interrogatory |
| 236 | Record Failure |
| 237 | Deathclock monitor |
| 238 | Recorder |
| 239 | Cigarette Inventory |
| 240 | Question |
| 241 | Failure Path |
| 242 | Listen for Receive Tone |
| 243 | Receive Tone Recognition |
| 244 | Playback |
| 245 | Decrement |
| 246 | Loop |
| 247 | Give Tone Recognition |
| 248 | Increment |
| 249 | Question |
| 250 | Listening Interval |
| 251 | Correct Answer |
| 252 | Correct Register |
| 253 | Incorrect Register |
| 254 | Dollar Bill Slot |
| 260 | BEDTIME module |
| 270 | Memory address port A0 |
| 271 | Memory address port A1 |
| 272 | Memory address port A2 |
| 273 | Memory address port A3 |
| 274 | Memory address port A4 |
| 275 | Memory address port A5 |
| 276 | Memory address port A6 |
| 277 | Memory address port A7 |
| 278 | Memory address port A8 |
| 279 | Memory address port A9 |
| 280 | Memory address port A10 |
| 281 | Memory address port A11 |
| 282 | Memory address port A12 |
| 283 | Memory address port A13 |
| 284 | Memory address port A14 |
| 285 | Memory address port A15 |
| 286 | Memory address port A16 |
| 287 | Memory address port A17 |
| 288 | Memory address port A18 |
| 301 | Electrical Circuit (Normally Open) |
| 302 | First Electrical Lead |
| 303 | Second Electrical Lead |

Referring to FIGS. 1, 2, 3 and 12, a smoking simulation apparatus 1 is shown which is housed in a case 2 which approximates the rectangular shape and dimensions of a package of cigarettes. The case 2 is formed of a plastic or metallic material and houses the mechanical and electrical components which comprise the active components of the device. Analogously, the embodiment for other drug deterrence purposes might take the form of a package of hypodermic needles or other drug-related paraphernalia. The intent is to provide some sense of connection in the mind of the user between the deterrence device and the addiction or habit being deterred.

On the front 5 of the enclosure 2 are grills (unnumbered) for the speaker 9 and microphone 10, which are mounted inside. The grill for the microphone 10 consists of two parts. First there is the central receptacle 8 for the straw portion 165 of the simulated cigarette 17 to fit into. This is the also primary opening for the microphone 10 to listen to speech and other sounds from the outside world. Second, the peripheral holes 13 surrounding the central receptacle 8 form jets of air 82 which impinge on the microphone 10 when the user (not shown) puffs through the simulated cigarette 17. The jets of air 82 impinging directly on the microphone 10 create a relatively loud white noise which is recognizable as a puff by the sound recognition software.

An alternative embodiment also includes an LCD alphanumeric or graphics display 32 for communicating silently to the user. The LCD display 32 might show a pictorial representation of a cigarette as it is being smoked by the user, showing it getting shorter. Simultaneously, the LCD display 32 might show a deathclock, showing average life expectancy lost if present rate of smoking continues, counting up in realtime as the user smokes. And the LCD display 32 can display textual information to the user, educating them on other aspects of smoking.

The top 6 of the enclosure flips opens like a hardpack of cigarettes. Inside the top 6 of the enclosure are pushbuttons for the user (student) 163 or supervisor (teacher) 179 to awaken the microprocessor 19. There is also an earphone jack 16 for communicating without disturbing those in the vicinity (such as in a classroom). The fliptop 6 also protects the buttons 163, 179 from being pressed inadvertently, and keeps the earphone jack 16 clean of dirt or pocket lint, since the device 1 is intended to be carried in a shirt pocket or purse (not shown).

The side 18 of the enclosure 2 has a recess 11 to hold a simulated cigarette or puffing device 17. The puffing device 17 is held externally so its storage area 11 can be easily cleaned with an alcohol swab for sanitary purposes.

Figure 13:
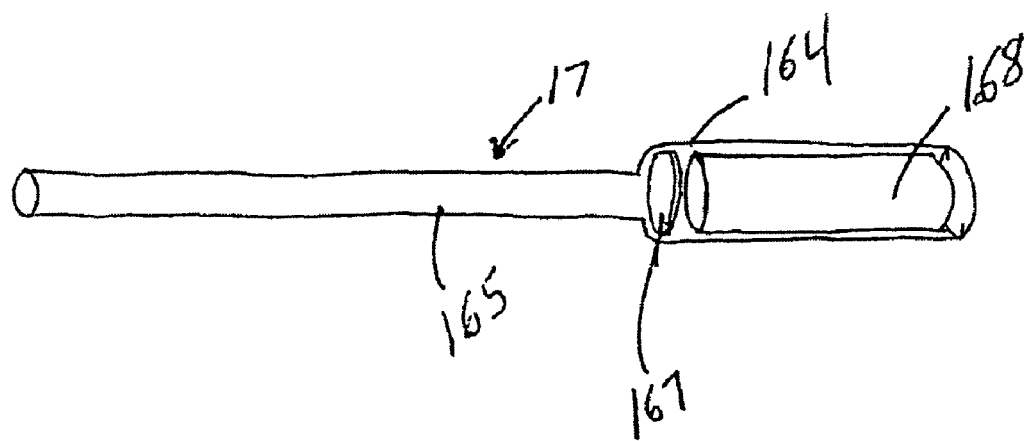
FIG. 13 is a perspective view of a second embodiment of a puff receptacle associated with the present invention.

Referring also to FIG. 13, the puffing device 17 can include a flow restriction to portion 164. The simulated cigarette or puffing device 17 has three main features: (a) a straw portion 165 that fits into the receptacle 8 on the enclosure 2, (b) a check valve 167 that prevents the user from blowing into the receptacle 8 and to keep the receptacle 8 clean for sanitary reasons, and (c) fixed or removable filter 168 that acts as a flow restriction to simulate actual puffing resistance of typical cigarettes, as well as puffing difficulty caused by lung disease. A similar straw can also simulate inhaling cocaine and methamphetamines. An alternative embodiment for deterring other drugs replaces the simulated cigarette 17 with a simulated hypodermic (without the needle) that emits an inaudible but recognizable whistle when "injected." The microphone 10 and software would hear and recognize the whistle and record that sound as an injection event.

Figure 4:
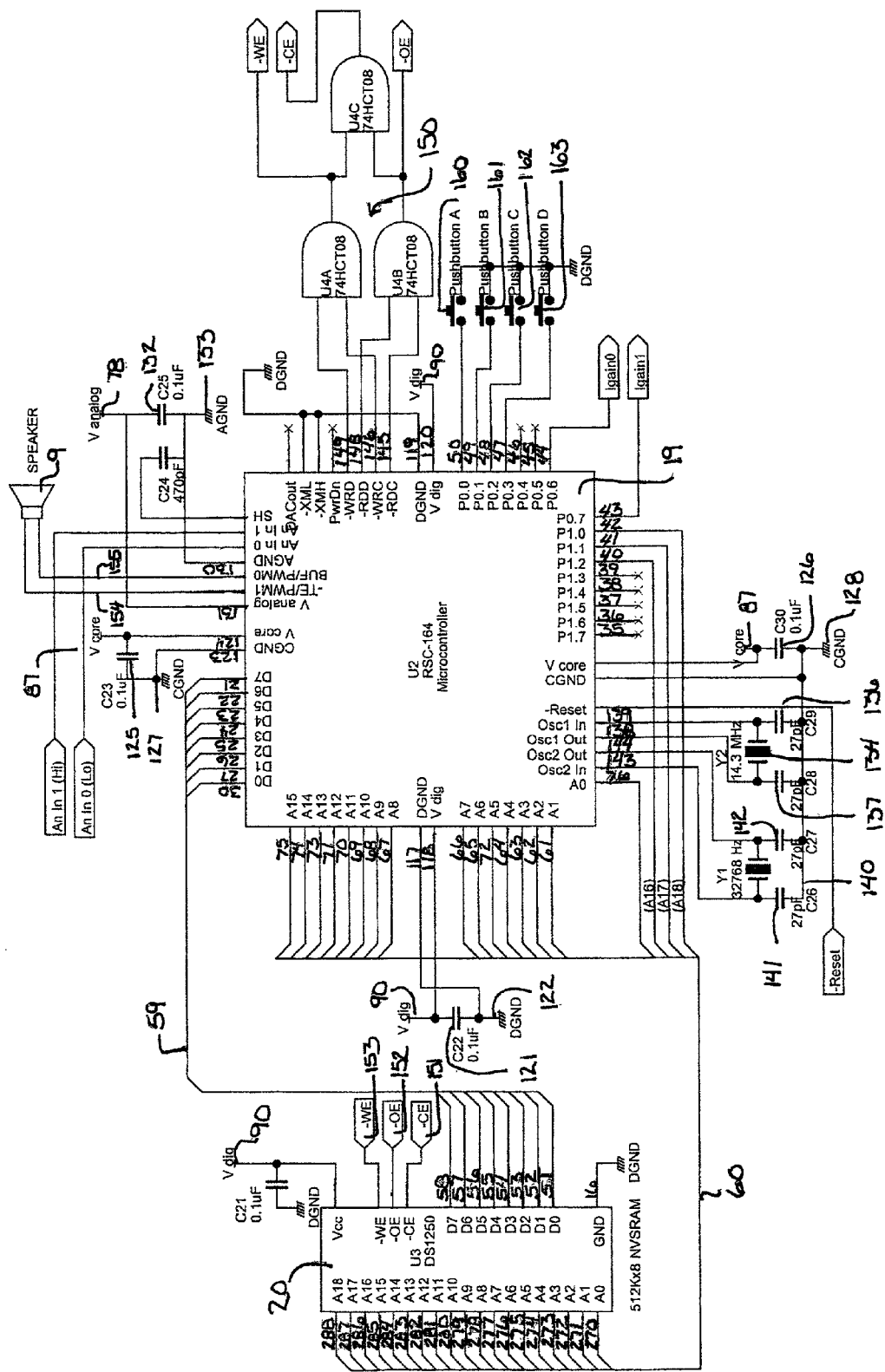
FIG. 4 is a schematic diagram of a portion of the present invention which includes a microprocessor and random access memory.

Referring to FIG. 4 some of the electronics of the present invention 1 can be appreciated. The simulator 1 is capable of both sensing sounds made by the user, such as coughing and inhaling, as well as generating spoken messages which instruct the user of the device. The speech recognition and speech synthesis functions are performed by integrated circuit 19, which is preferably an RSC-164 Microcontroller and speech processing circuit manufactured by Sensory, Incorporated, 521 East Weddell Drive, Sunnyvale, Calif. 94089. The specific function and features of circuit 19 are more fully described in U.S. Pat. No. 5,790,754, issued to Mozer et al. The circuit 19 is powered by three isolated power supplies and ground reference levels. Power source 90 supplies digital Input/Output pins 117, 118, 119 and 120. Filtering is accomplished by capacitor 121 and digital ground connection 122. Core power supply 87 supplies core processing via pins 33, 34, 123 and 124. Filtering is accomplished by capacitors 125 and 126, and core ground connections 127 and 128. Analog power supply 78 furnishes power for audio processing via pins 130 and 131. Filtering is accomplished by capacitor 132 and ground connection 133. Processing speed is controlled by a high speed oscillator network composed of crystal 134, capacitor 136 and capacitor 137, which are connected to oscillator pins 138 and 139. A low speed oscillator network consisting of crystal 140 and capacitors 141 and 142 is attached to microcontroller 19 at pins 143 and 144.

The circuit 19 includes sixteen general purpose Input/Output ports 35-50. Each pin can be programmed as input with a weak pull up, an input with a strong pull up, an input without pull up or as an output. Microcontroller 19 also includes an external memory interface that allows connection to a standard nonvolatile static random access memory chip 20. Microcontroller 19 includes separate read and write signals for each external memory space. Microcontroller 19 is constructed with eight data input/output lines 21-27 and 30, which are interconnected to the corresponding data input/output lines 51-58 via data bus 59. Addressing is accomplished along address bus 60. In this particular use of the microcontroller 19, sixteen address lines (61-76) and three general purpose I/O ports configured as address lines (40-42) are used to address 512 kilobytes of memory stored in memory chip 20. The nineteen address lines are connected to pins 270 through 288 of memory chip 20. The microcontroller 19 controls memory access via pin 145 (read code), pin 146 (write code), pin 148 (read data) and pin 149 (write data). These pins are ANDED together by integrated circuit 150 to provide appropriate logic control to control memory chip 20, the latter being controlled by pin 151 (chip enable), pin 152 (output enable) and pin 153 (write enable). The data written to or received from memory chip 20 is transferred via the data bus 59 to connecting pins D0-D7 of microcontroller 19 and connecting pins 51-58 of the memory chip 20. Audio output is provided via speaker 9 which is attached to the pulse width modulation output pins 154 and 155 of the microcontroller 19.

Figure 10:
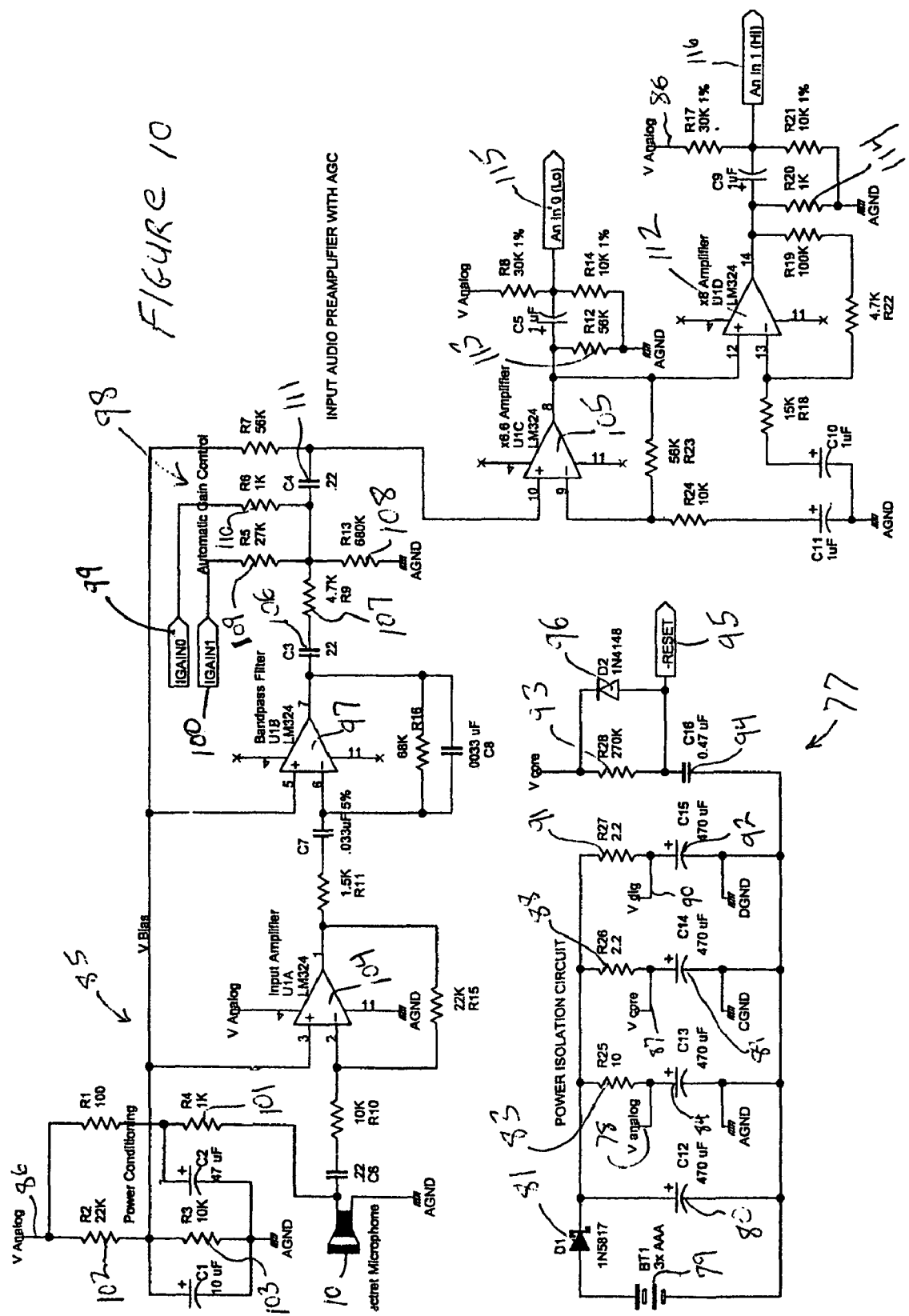
FIG. 10 is a schematic diagram of a preamplifier and power supply constructed according to the principles of the present invention.

Referring to FIG. 10, the power supply 77 includes three separate power supply elements. The analog power supply 78 receives its input power from system battery supply 79 which is preferably formed from three "AAA" alkaline batteries wired in series. Capacitor 80 and diode 81 form a half wave rectifier or filter which also protects the remaining circuitry against incorrect (reverse polarity) battery insertion. Analog power supply 78 is isolated and filtered by resistor 83 and capacitor 84. The analog power supply 78 provides power to audio preamplifier 85 via terminal 86. The core power supply 87 is isolated and filtered by resistor 88 and capacitor 89. Core power supply 87 provides power to microprocessor 19. The digital Input/Output power supply 90 is isolated and filtered by resistor 91 and capacitor 92. The power source 90 provides power to memory chip 20. The resistor 93 and capacitor 94 form an RC network with a time constant of approximately 0.1 second, thereby permitting transients to decay prior to the application of power to RESET terminal 95. This ensures a clean reset and start of microcontroller 19 into an electrically stable environment. Diode 96 discharges capacitor 94 in the event of a major core power supply 87 transient, thereby providing for a reset of microcontroller 19 if such a transient occurs.

The audio preamplifier 85 is a four stage amplifier with a bandpass filter 97 and with a two bit automatic gain control circuit 98 as specified in the Sensory, Incorporated manual for the RSC-164 Development Kit. When terminals 99 and 100 are set for a high impedance input, the maximum gain is approximately 59 decibels at the center frequency of 1.49 KiloHertz. This is a gain for a typical application with the microphone about 1.0 to 1.5 feet from the user in a quiet environment. This may vary depending on the ambient environment. The 3 decibel cutoff frequencies are 580 KiloHertz and 4.2 KiloHertz. Resistor 101 supplies the power to a standard two wire electret microphone 10. The voltage divider resistors 102 and 103 are used to provide the DC bias for amplifier stages 104, 97 and 105, and is set to approximately one third of the voltage appearing at terminal 86. The first stage 104 has a gain of approximately 2.2. The bandpass filter 97 has a gain of approximately 7.8 at the center frequency of 1.49 KiloHertz. The two bit AGC circuit 98 is a programmable voltage divider consisting of Capacitor 106, resistor 107, resistor 108, resistor 109, resistor 110, and capacitor 111. In order to prevent DC level shifts in response to AGC changes, the AGC circuit 98 is AC coupled by capacitor 106 and capacitor 111. The AGC input control signals appearing at terminals 99 and 100 may independently be either at ground or at high impedance, giving four different levels of attenuation. The gain ratios for the AGC circuit 98 are 1.0, 0.36, 0.18 and 0.13. The third stage amplifier 105 has a gain of 6.6, while the fourth stage amplifier 112 has a gain of 8. Resistors 113 and 114 provide adequate output bias current to prevent crossover distortion between third stage amplifier 105 and fourth stage amplifier 112. Both of the output terminals 115 and 116 are AC coupled and then DC biased such that at full swing the negative peak voltage goes below zero volts DC (analog ground) at the inputs of speech recognition microcontroller 19.

Referring again to FIGS. 1, 2, 3 and 4 there are several pushbuttons attached to the microcontroller 19 digital Input/Output ports (47-50). For example, a momentary microswitch 160 is activated by pushing a dollar bill into a slot 254 in the enclosure 2. The switch 160 detects the action of a user paying for their cigarettes. A bellows switch 161 is an alternative method of detecting puffs or inhalations on a simulated cigarette 17. The bellows switch 161 may also be replaced by a pressure sensor switch (not shown) which can perform a similar purpose. Sound activated switch 162, such as described in the Radio Shack catalog No. 276-5011A, is an alternative method of detecting either puffing on a simulated cigarette 17 or coughing. Similarly, the simulated cigarette 17 can be designed to produce an audible or subaudible whistle tone during puffing. The whistle tone can be sensed by the sound activated switch 162 tuned with a bandpass filter (not shown) encompassing the whistle tone frequency spectrum. A further option, shown in FIG. 19, is to incorporate a normally open electrical circuit 301 on the surface 17s of the simulated cigarette 17 with the circuit 301 in electrical communication with the battery 79 and the microcontroller 19 by electrical leads 302 and 303. The electrical circuit 301 is configured and arranged on the simulated cigarette 17 so that positioning of the simulated cigarette 17 between the lips (not shown), in simulation of actual smoking mechanics, closes the electrical circuit 301 and sends an appropriate signal to the microcontroller 19. The puffing sound activated switch can be eliminated by using a sound integrator or sound recognition software. In addition, the pushbutton 163 may be used to activate or awaken the microcontroller 19 when it is in a power saving mode.

Figure 5:
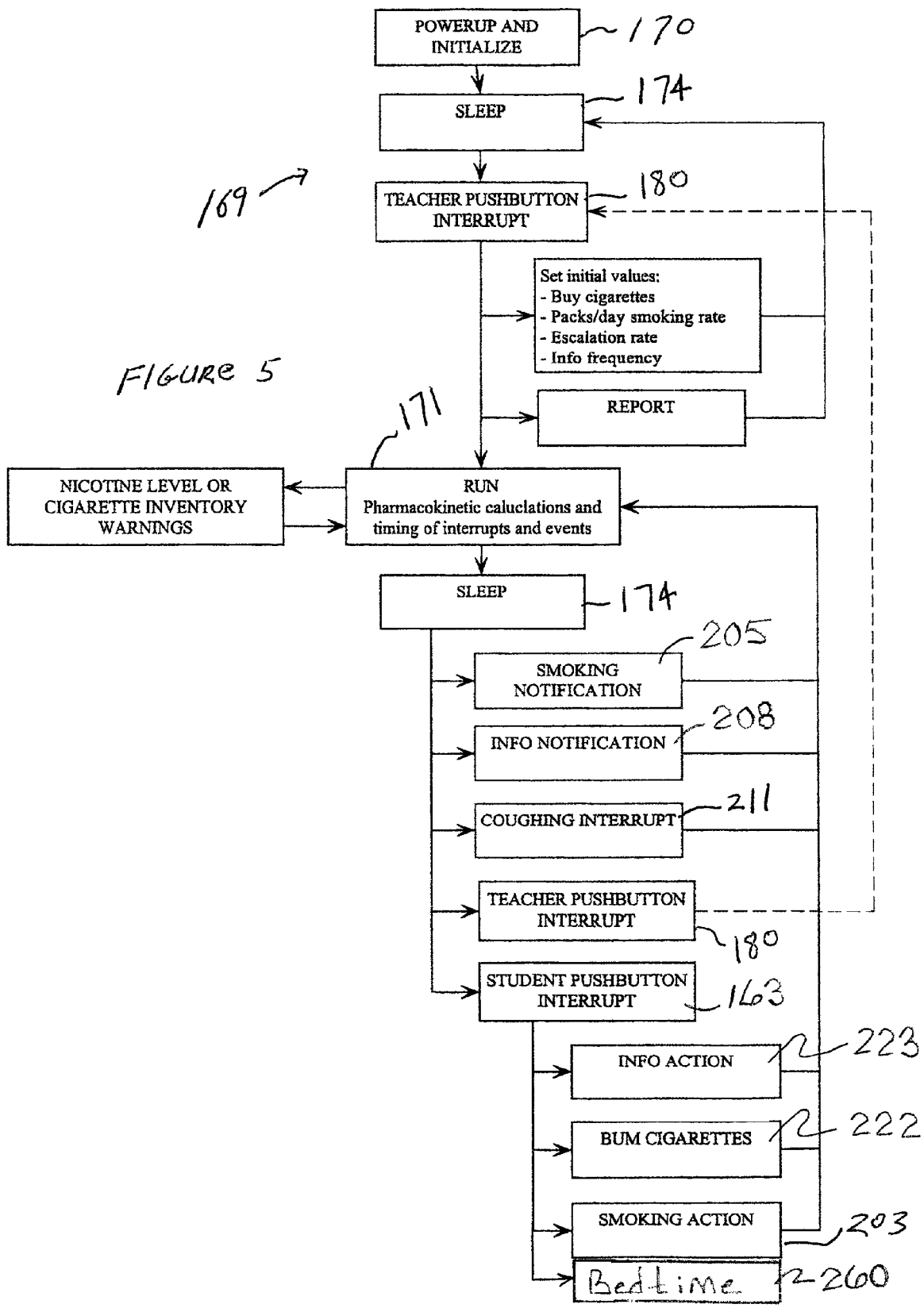
FIG. 5 is a flow chart depicting the general operation of the present invention.

The following narrative referring to FIG. 5 assumes that the smoking simulator 1 is used in a school environment. The "Teacher" is the person who sets up the device 1 for use by the "Student," and afterwards evaluates the student's performance by commanding the device 1 to produce a recorded report. The various software flowcharts presented here are separated into modules which are functionally distinct from each other. The overview flowchart 169 shows the general relationship between modules, and the logical sequence of the flow of instructions from module to module. Subsequent flowcharts illustrate the inner workings within each module.

In many of the flowcharts there are references to Sensory, Inc.'s proprietary software subroutines for various speech functions. Rather than explain them each time they are used, they are summarized here. Speaker Verification (SV) subroutines are used for storing and verifying passwords. SV subroutines can distinguish between individual speakers. Speaker Independent (SI) Recognition subroutines are used for recognizing specific commands or responses, no matter who says them. Speech Synthesis (SS) subroutines simply playback a prerecorded word, phrase, or lengthy message. Continuous Listening (CL) Recognition subroutines are used for recognizing specific commands or sounds that may occur at unpredictable times, and must be listened to for an extended period.

The software modules for the smoking simulation 1 are divided into two broad groups. The modules focusing on the teacher's activities start with POWERUP step 170. The student's activities begin with the RUN module 171. The teacher's activities configure the device 1 to recognize his or her passwords, provide the level of challenge they feel is appropriate and, after the simulation is completed, report the results of the student's use of the device 1. The student's activities include recording their passwords, responding to demands from the device 1 to cough or perform simulated smoking, and listening to extensive educational material. The student also has the option of bumming cigarettes from other students with similar devices 1 and placing the device 1 in BEDTIME mode 260. The active operating time of the device 1 is brief compared to the total time it is used, so it spends a large portion of time in SLEEP mode 174 to conserve battery power.

Figure 6:
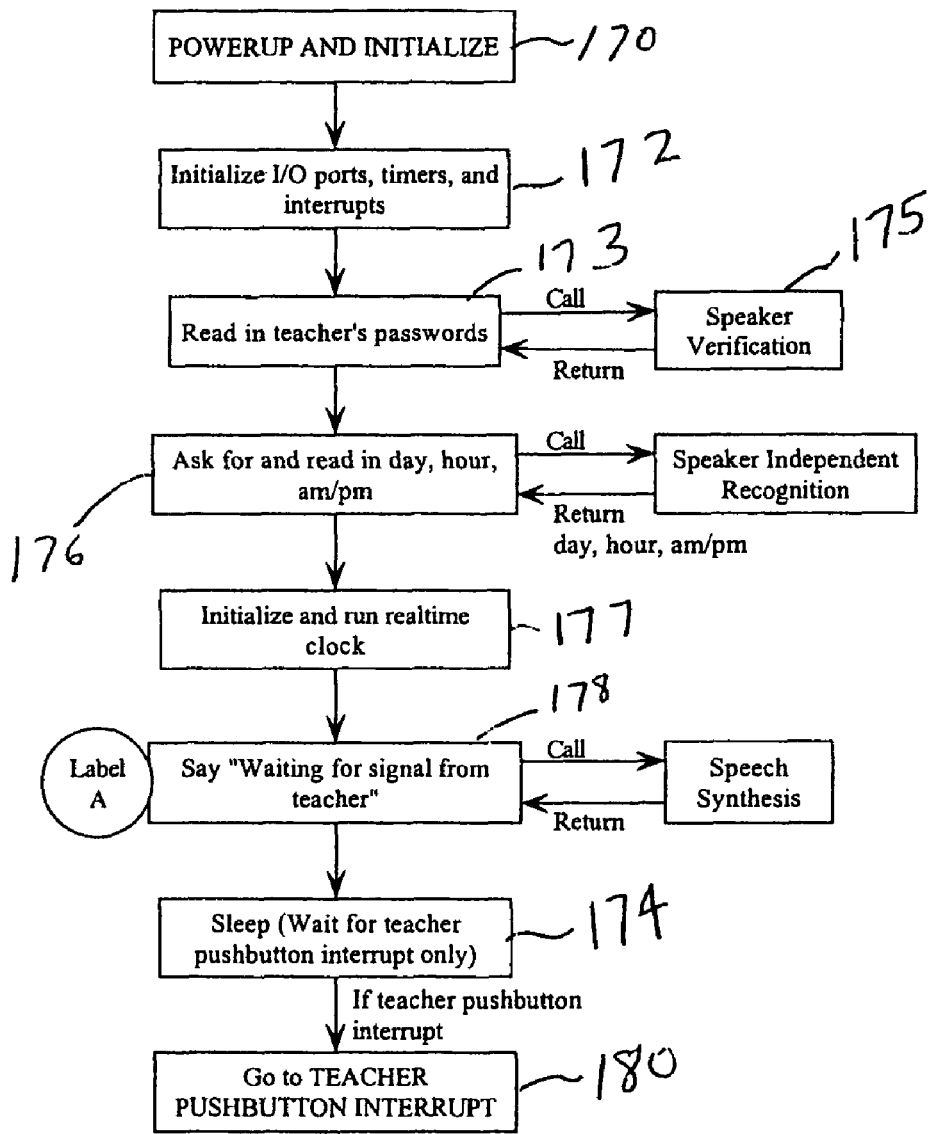
FIG. 6 is a flow chart depicting the POWERUP AND INITIALIZATION portion of the software depicted in FIG. 5.

Referring also to FIG. 6, when the battery 79 is connected, the microprocessor 19 must perform a "bootup" procedure 172 to properly configure timers, input/output ports, and interrupts. Otherwise they might initialize in a random configuration. Once these basic housekeeping activities are done, the microprocessor runs the applications program for smoking deterrence. There is no on/off or "reboot" switch. Those functions are accomplished by connecting and disconnecting the battery 79. So each time the battery 79 is reconnected, the software must request and store in step 173 the passwords from the teacher. In the preferred embodiment password security is twofold: (a) the teacher can keep their passwords secret and (b) the software recognizes in verification step 175 the voice patterns of the individual teacher, so it is difficult for a student to cheat even if they discover the teacher's passwords. The passwords are used to limit access to the subsequent simulation setup steps to the teacher alone. This precaution prevents the student from changing the conditions of the simulation.

A realtime clock, albeit not very accurate (say, plus or minus one hour), is needed to time some events for a specific part of the day. For example, as the exercise progresses to simulate more frequent smoking, the student may be awakened in the middle of the night to have a desperate smoke or have an extended coughing fit. Therefore the software asks for and stores the day and time of the start of the simulation at time entry prompt 176. The day is preferred because the software must report the total elapsed time of the simulation, and reporting the starting day and time is easier to understand than reporting simply the number of hours elapsed.

Alternatively, the scheduling of events each day, such as smoking the first cigarette of the day and the late evening coughing fit, can be based upon the bedtime schedule established by the student, wherein the end of the bedtime period is used as the beginning of the daily schedule (e.g., eight hours after the student initiated the bedtime period the daily schedule commences and continues until the student again activates a bedtime period).

With the realtime clock initialized and running at clock startup step 177, the device 1 can go to sleep and wait for the teacher to wake it up for further instructions to proceed with the student's portion of the software. Prior to entering SLEEP mode 174, device 1 tells the teacher that it is awaiting their signal at prompt step 178. This notification to the teacher is an attempt to make the device 1 user friendly and self-documenting.

Figure 7:
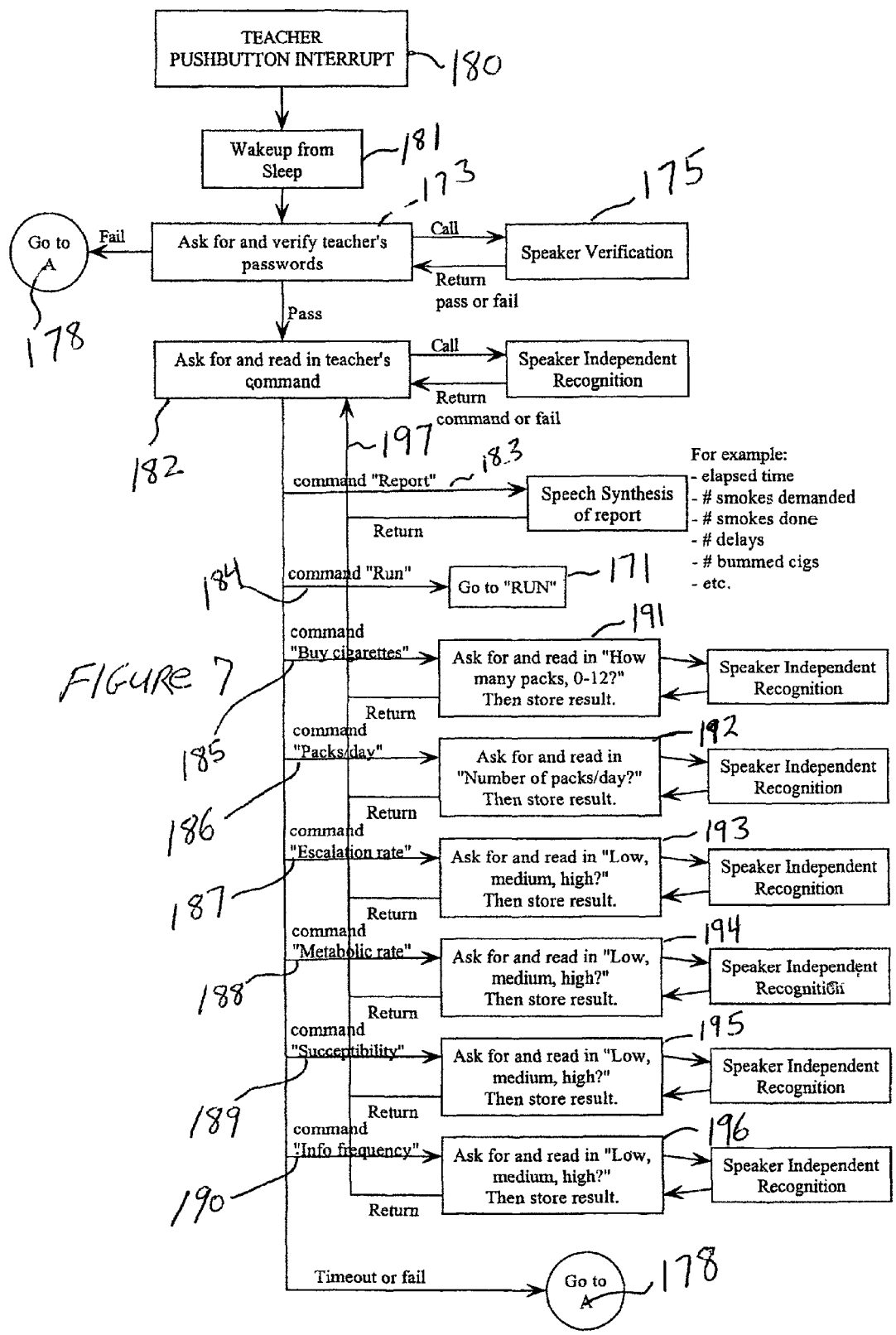
FIG. 7 is a flow chart portraying the TEACHER INTERRUPT portion of the software referred to in FIG. 5.

Referring also to FIG. 7, the teacher awakens the device 1 by pushing at interrupt step 180 a wakeup button 179 which can be labeled "Teacher." Upon completing wakeup step 181, the device 1 will verify that it is indeed the authorized teacher who is responsible for the activation by asking for and verifying the teacher's password at step 173. If password verification fails, the software returns to the step 178 in the POWERUP module to notify the teacher that it is going to sleep to await a valid wakeup call. If the teacher's passwords are correctly verified, the software asks the teacher via request 182 to state one of several commands, such as Report 183, Run 184, Buy Cigarettes 185, Packs Per Day 186, Escalation Rate 187, Metabolic Rate 188, Susceptibility 189, or Information Frequency 190. If command recognition fails, the software returns to the step 178 in the POWERUP module to notify the teacher that it is going to sleep to await a valid wakeup call, just as it would if password verification failed. If the teacher commands Report 183, the device 1 will recite the appropriate measurements of the student's activity with the device 1. A few examples of data included in the report recitation are elapsed time, number of cigarettes demanded, number of cigarettes consumed, number of delays in responding to demands to smoke, number of delays in responding to demands to cough, and number of cigarettes borrowed. If the teacher commands Run 184, the software will jump to the RUN module 171 where the student-related software begins.

The day-to-day monetary cost of smoking is one of its aspects simulated by the device 1. The device 1 keeps track of an imaginary inventory of cigarettes, decrementing the inventory whenever the student smokes, and incrementing the inventory whenever the student "purchases" more from the teacher. The software can be programmed to track the cost of the cigarettes purchased and/or smoked for use in educating students about the financial aspect of smoking. Therefore, when the teacher commands Buy Cigarettes 185, the software will ask at step 191 for the teacher to set the number of packs of cigarettes available to the student before more must be purchased. The upper limit is high enough that it is effectively unlimited, in case the teacher does not want a limit.

The software has several other variables which can be set by the teacher to tailor the simulation to their needs. The initial level of addiction can be set by commanding an initial smoking rate 192 in packs per day. The teacher also sets the escalation rate 193, that is, how many days it takes to escalate from one pack per day to two or three or four packs per day. This will often depend on how long the student can keep the simulator before it must be used by someone else, and how rigorous a lesson the teacher wants the student to endure. For example, the medium settings simulates a one pack a day habit on the first day, two packs a day on the second day, and three packs a day on the third day.

The student's physiological response to nicotine is simulated by gathering and setting a data point of the student for a variable recognized as influencing a persons physiological reaction to nicotine, such as metabolic rate 194 and susceptibility 195. These variables are described in the curriculum literature that accompanies the device 1. In general, these variables are dependent on the student's level of physical activity (active or inactive) and body weight.

The rate of educational information 196 recited to the student can also be set by the teacher. If the teacher sets the simulation to last only one day, the goal will typically be to inundate the student with a rapid rate of information 196. If the simulation is intended to last a week, the information rate 196 may be reduced to a relatively meager rate.

After each variable has been set by the teacher, the program returns via path 197 to ask the teacher to give another command. When the teacher finishes setting as many variables as they wish, the teacher will respond to the request for command with silence or a noncommand word. The software will then return to idling step 178 in the POWERUP module and notify the teacher that the device 1 is going to sleep.

Figure 8:
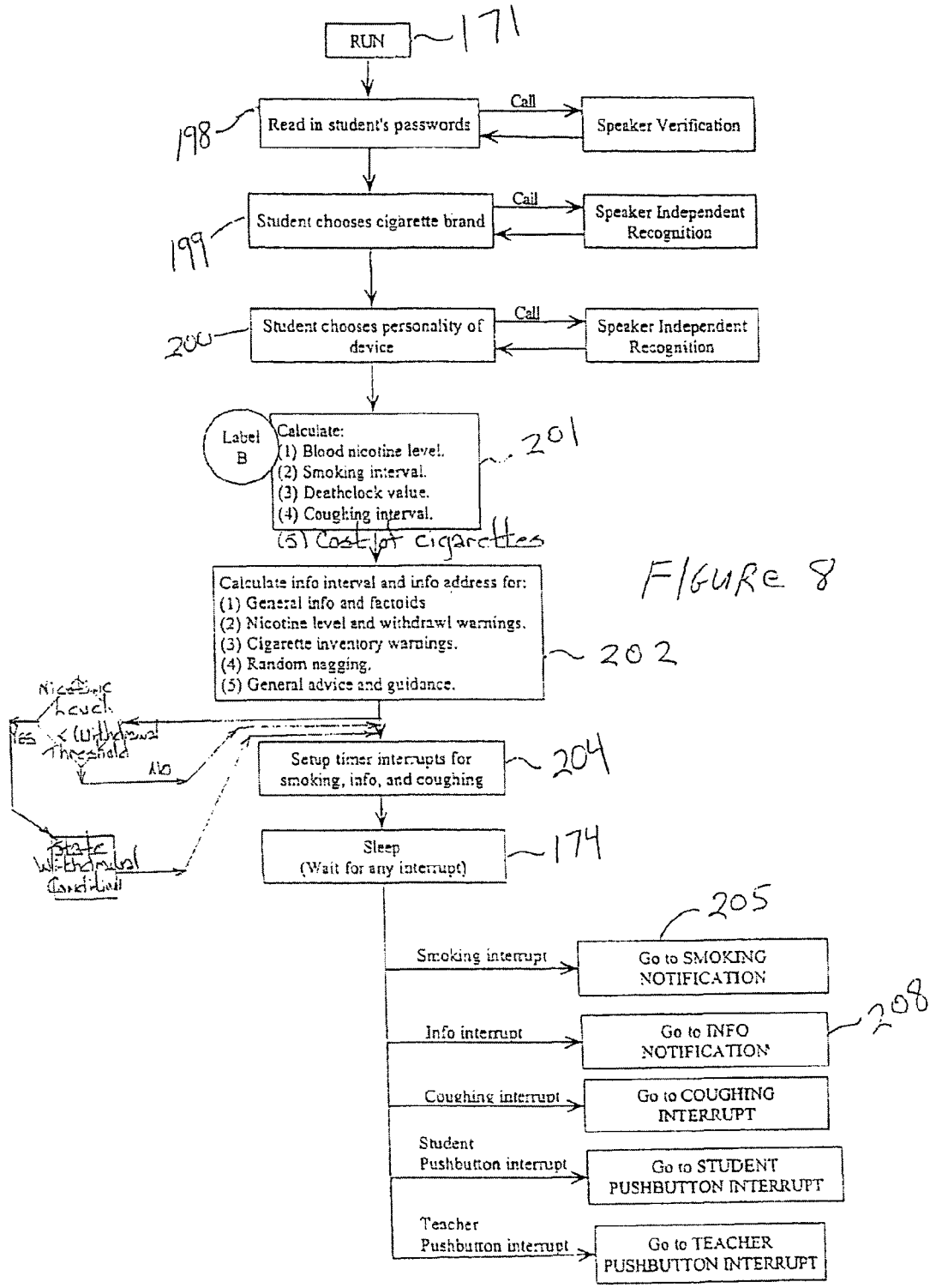
FIG. 8 is a flowchart of a portion of the present invention which portrays the RUN subroutine.

Referring also to FIG. 8, the RUN module 171 is an "Executive" routine because it performs calculations, checks lookup tables, and otherwise makes decisions that affect the course of events throughout the student's use of the device 1. Most of the other modules in device 1 merely respond to calls from interrupts or from the RUN module 171. The RUN module 171 is the only module that makes activity scheduling decisions. Throughout the simulation, the device 1 will make demands of the student, await the student's response, and measure and record that response for eventual reporting to the teacher. Each time the student responds to a demand, the device 1 will verify that the response is coming from the correct student (the student to which device 1 was assigned). This keeps the students honest and prevents them from giving the device to, for example, a little brother, to play with. An added benefit is that when the student knows they cannot cheat, they pay closer attention.

To enable verification of the student's identity, the device 1 as a first step 198 records a student's password. The verification step 198 of the software can only be accessed immediately after the teacher executes Run command 184, so the teacher will be present to ensure that the designated student records their voice-dependent password. Once this is done, the student cannot access verification step 198. The passwords can only be changed by the teacher, using their own passwords, or by removing the battery 79, which is detectable by the teacher since it will affect the realtime clock 177 as well as the teacher's passwords.

The student is given some choices to tailor the simulation to their personal preferences, which will hopefully give the student a greater interest in the results. First the student selects at step 199 a brand of cigarettes. Each brand will have its own market appeal, cost, nicotine content, and carcinogenic effect, which will be recorded in the device's memory 20, and will be used in calculations that follow. The student next chooses a personality 200 for their device. The personality 200 traits apply to only a few of the messages from the device 1, but are hopefully frequent enough to keep the student interested and paying attention. Personality 200 traits include Humorous, Sarcastic, Motherly, Scientific, Suggestive, Teenage or Random.

The core of the simulation scheduling software resides in the next two steps 201 and 202 which calculate the realistic physiologic effects on the student of the simulated nicotine addiction defined by the values the teacher has previously set for the simulation variables. This includes calculation 201, using equations from actual pharmacokinetic studies, of the student's simulated blood nicotine content using variables such as: (a) how long ago did they last smoke a cigarette, (b) what brand of cigarette was it (nicotine contents vary), (c) how fast did they smoke it, (d) how completely did they smoke it, (e) how fast do they metabolize nicotine, (f) what is their physiologic susceptibility to blood nicotine level, and (g) what time of day is it (metabolic rates vary).

From these physiological calculations 201, the software will assign a simulated nicotine craving level 202 to the student. This craving level 202 ranges from mild agitation through many levels of anxiety and irritability all the way up to immobilizing nausea. This craving level 202 will be communicated to the student in several ways: (a) demands for a smoke, (b) nicotine level warnings, (c) general information and factoids, (d) detailed descriptions of how they would feel and demands for how they should act, (e) random and escalating nagging, and (f) general advice and guidance. Based on the student's simulated craving level 202, the software will decide by using a series of lookup tables the appropriate level of intensity of educational messages at any given time during the simulation, and select the addresses within electronic memory 20 of the messages to playback to the student. Alternatively, the software can be programmed to generate a smoking demand signal whenever the calculated blood nicotine content falls below a defined minimum threshold value.

In the extreme case where a student excessively delays smoking to the point of withdrawal, such as determined by the calculated blood nicotine content falling an additional amount below the defined minimum threshold value, or determined by the time interval between generation of a smoking demand and the detection of a simulated smoking action exceeding a threshold value, the software can inform the student that the student has entered withdrawal and/or demand a vomiting episode once the long delayed cigarette is finally smoked in which the student must make a retching noise that the software can recognize. The vomiting episode activity is scheduled in the nicotine craving level step, although it is actually performed in the SMOKING ACTION module 203.

As the simulation progresses to higher levels of addiction and more frequent smoking, the calculated physiologic effects 201 will escalate, and the simulated damage to the student's lungs will accumulate. Part of this calculation is based on the carcinogenic effect of the cigarette brand chosen by the student. As a result, the device 1 will generate more frequent and more severe messages, such as demands to smoke, demands for coughing fits from the student, an indication that the student just vomited, and an indication that the student is suffering from an anxiety attack, eventually to the point of waking the student up in the middle of the night to cough, smoke, and cough some more. By way of example, when the software is programmed to generate a smoking demand signal whenever the calculated blood nicotine content falls below a defined minimum threshold value, an escalation in the frequency of the smoking demand signal (i.e., a decrease in the time interval between sequential smoking demand signals), representative of the development of tolerance for nicotine, can be achieved by incrementally increasing the minimum threshold value as a function of the number of simulated cigarettes the student has smoked during an assignment period. Alternatively, the software can be programmed to generate a smoking demand signal at predetermined intervals throughout an assignment period wherein the interval between sequential smoking demand signals is diminished over time in a gradual or step-wise fashion for purposes of representing the development of tolerance for nicotine. While not preferred, it is, of course, also possible to program the software to simply provide intervals between smoking demand signals which are of substantially identical duration (e.g., each interval throughout an assignment period is 55 minutes) or of varying and patternless duration (e.g., sequential intervals of 20, 55, 90, 25, 20, 60, 35, 15, etc.).

Other information that may be calculated and communicated to the student includes the monetary cost of the cigarettes smoked, pulse rate variations, lung capacity reduction, blood pressure increase, stress on the heart, and other diseases or conditions to which smokers may be susceptible because of their smoking. The software will update the value of a "Deathclock" that measures the expected minutes/days/years of lifespan lost assuming that the current trend of simulated smoking proceeds unchecked. The deathclock is calculated by nicotine craving level block 202 but reported in the SMOKING ACTION module 203, immediately after the student smokes, to give the student immediate feedback on the long term consequences of their smoking.

Once the nicotine craving block 202 has calculated what messages regarding smoking, coughing, and educational information should be communicated to the student, and when they should be communicated, the software will setup internal timers 204 to wake itself up at the appropriate times. The device 1 will go to sleep and wait for those interrupts. Once asleep, device 1 will also respond to pushbutton interrupts from either the student or the teacher.

Figure 9:
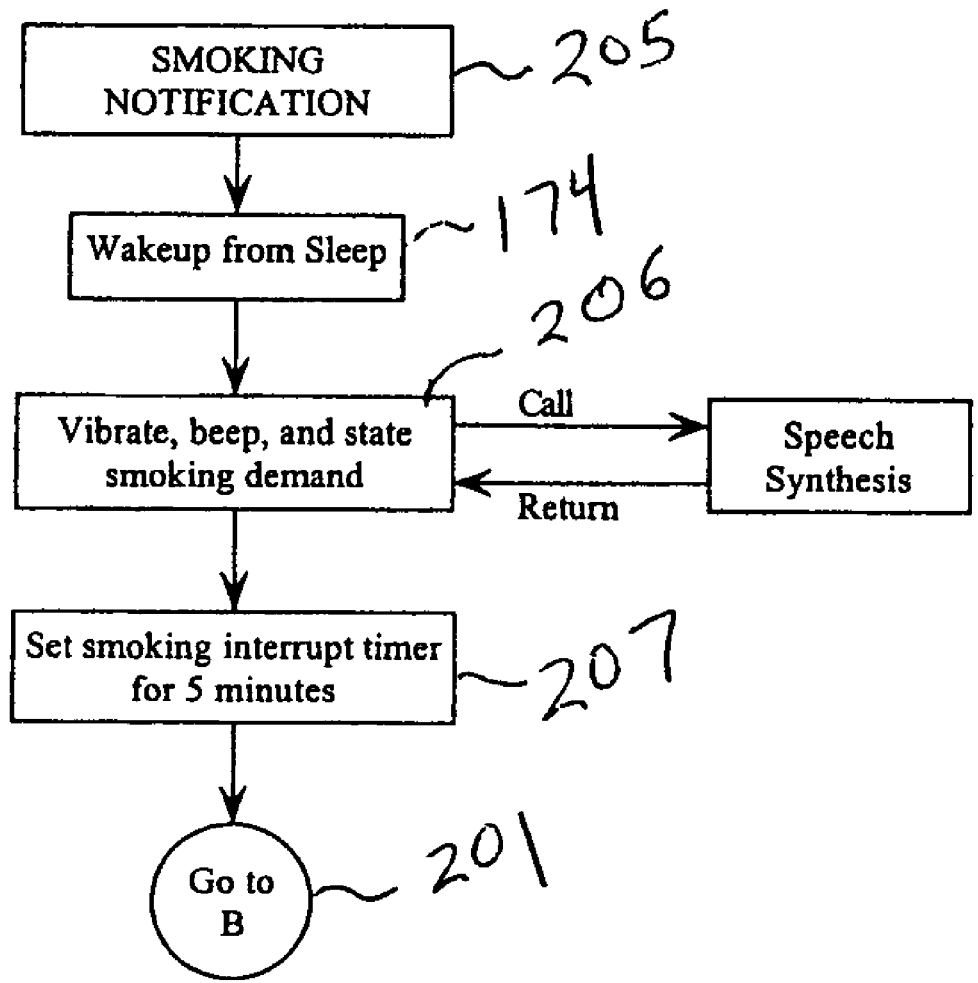
FIG. 9 is a flowchart of a portion of the present invention which portrays the SMOKING NOTIFICATION subroutine.

Referring also to FIG. 9, the SMOKING NOTIFICATION module 205, which is called by the RUN module 171, simply notifies the student that it is time to smoke. The student must respond via the Student Pushbutton 163 before simulating smoking. Simulated smoking is processed by the SMOKING ACTION module 203. The device 1 has three notification methods 206 of notifying the student that it is time to smoke. There is a pager-type vibrator that the student can feel if the device is in their pocket. There is a beeper-type beep that the student can hear if the device is in their purse or if they are asleep. Finally, after a short pause, there is a spoken demand for smoking. After notifying the student, the device scheduler 207 sets the next notification for five minutes in the future. Alternatively, the perceptible notice can be generated continuously until terminated by detection of simulated smoking by the student. This ensures an irritating nagging process for as long as the student puts off smoking. Then the software returns to calculator 201 and nicotine craving block 202 in the RUN module 171 to recalculate the student's simulated nicotine level and craving level based on the extra time elapsed, and then returns to SLEEP mode 174.

Figure 11:
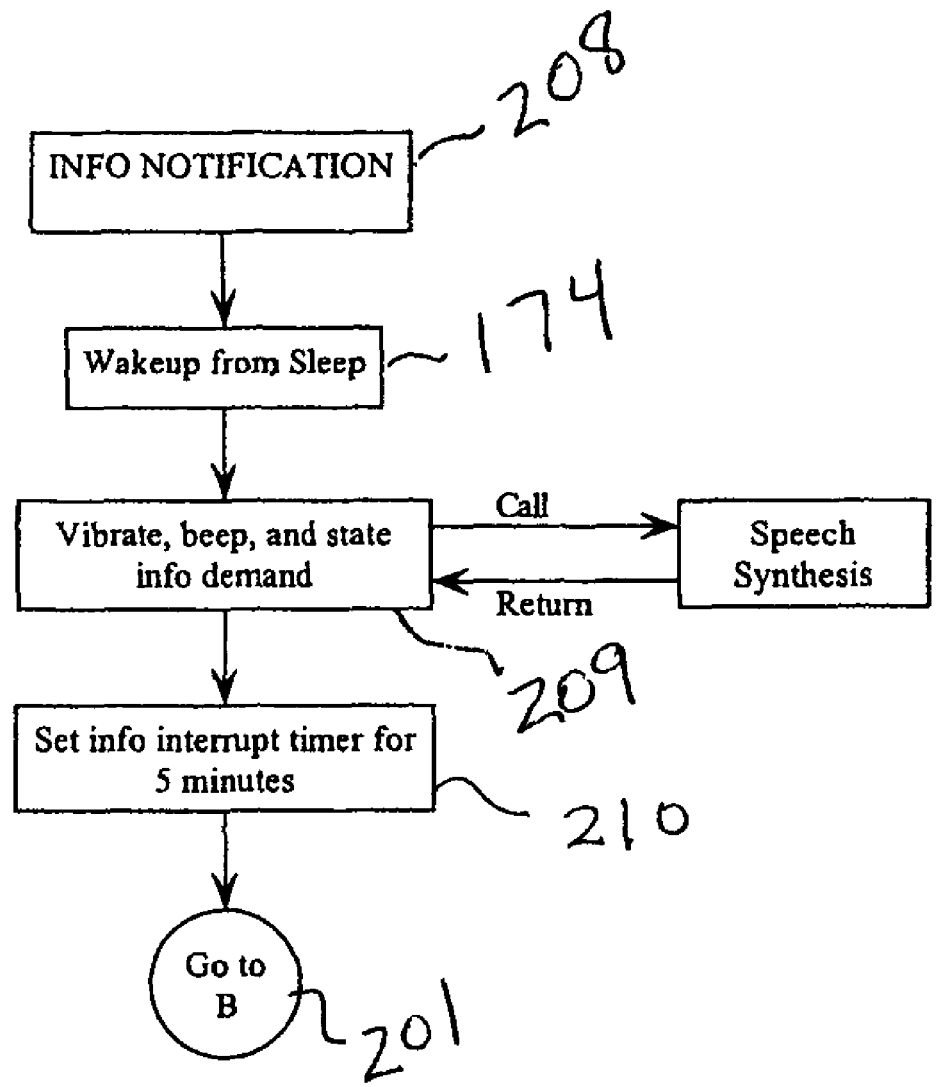
FIG. 11 is a flowchart depicting the INFORMATION NOTIFICATION subroutine utilized by the present invention.
Figure 12:
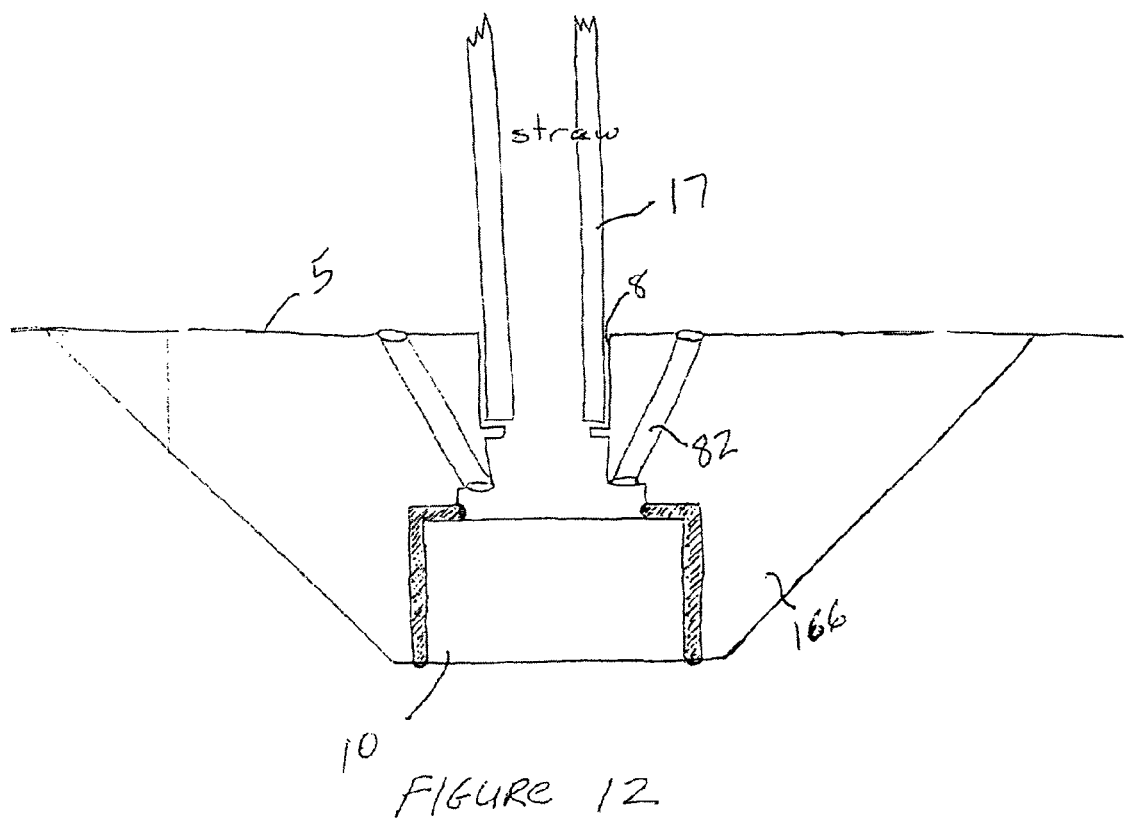
FIG. 12 is a side sectional view of one embodiment of a puff receptacle and sensor associated with the present invention.

As seen in FIG. 11, the INFORMATION NOTIFICATION module 208, which is called by the RUN module 171, simply notifies the student that it is time to listen to educational information, including information regarding the occurrence of voluntary (i.e., unscheduled trip to the market to purchase cigarettes) and involuntary (i.e., coughing and vomiting) addiction-induced physical actions. The student must respond via the Student Pushbutton 163 before listening to the information. The device 1 has three methods 209 of notifying the student that it is time to listen to information. There is a pager-type vibrator that the student can feel if the device is in their pocket. There is a beeper-type beep that the student can hear if the device is in their purse. And finally, after a short pause, there is a spoken demand for the student to listen to information. After notifying the student, the device 1 sets the notification timer 210 for five minutes in the future. This ensures an irritating nagging process for as long as the student puts off listening to the information. Then the software returns to the calculation 201 in the RUN module 171 to recalculate the student's simulated nicotine level, craving level and message intensity level based on the extra time elapsed. The device 1 then enters SLEEP mode 174.

Figure 14:
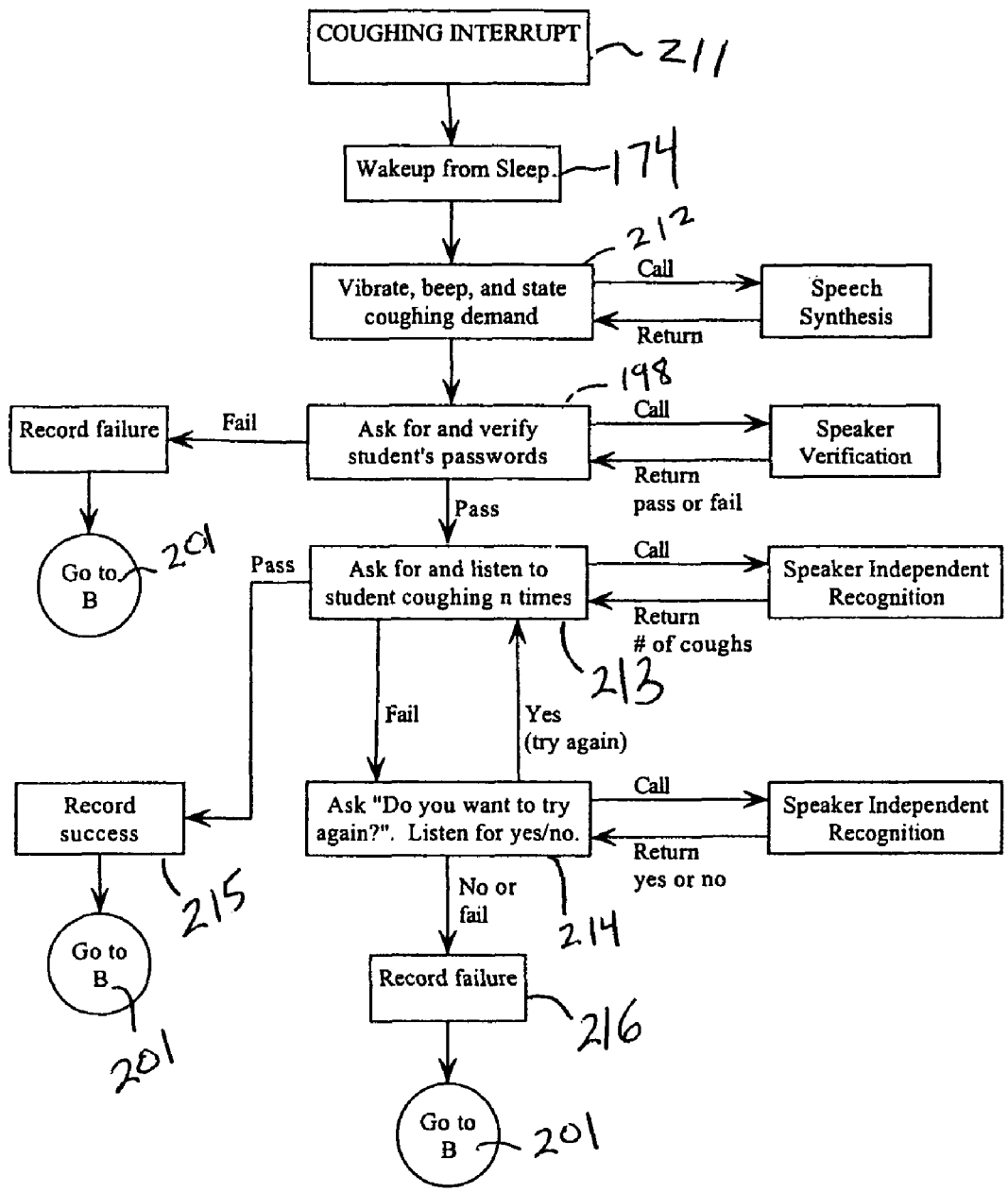
FIG. 14 is a flowchart depicting the COUGHING INTERRUPT subroutine utilized by the present invention.

As seen in FIG. 14, the COUGHING INTERRUPT module 211, called by the RUN module 171, both notifies the student that it is time to cough, and monitors whether they do or do not cough. This action cannot be delayed, only passed or failed. The Student Pushbutton 163 is neither required nor active when module 211 is active. The device 1 has three methods 212 of notifying the student that it is time to cough. There is a pager-type vibrator that the student can feel if the device is in their pocket. There is a beeper-type beep that the student can hear if the device is in their purse. And finally, after a short pause, there is either a spoken demand for coughing or loud playback of a recorded cough. Alternatively, the perceptible notice can be generated continuously until terminated by detection of the requested coughing action by the student. In order to awaken students in the middle of the night, the device 1 may playback a coughing fit rather than a spoken demand. After notifying the student, the device 1 initiates verification step 198 by asking for the student's passwords, thereby making sure that the right student will be coughing.

The RUN Executive routine 171 will pass a parameter to COUGHING module 211 specifying the demanded intensity of the coughing episode. The parameter may specify anything from a single hack to an extended coughing fit. The COUGHING module 211 will at cough prompt 213 ask for, listen for, and recognize the student coughing some specified number of times. If the student fails to cough appropriately, the device will give them the option 214 to try again. Their success 215 or failure 216 will be noted before returning to the RUN module 171 for recalculations 201 and the return to SLEEP mode 174.

Referring also to FIG. 15, after the student has been notified that the device demands either smoking or information playback, the student can press the Student Pushbutton 163 to indicate that they are ready to perform the demanded action. This wakes the device 1 up from the SLEEP mode 174. After awakening, the device 1 asks for and verifies at step 198 the student's passwords to make sure that the correct student has awakened the device 1. Next, the device 1 asks for the student's command 217 to either smoke, bum cigarettes, or playback educational information. At this point, depending on student delays, random chance generator 218, and recognition by the software of extraneous epithets, the software may select belligerence path 219. For example, the software may randomly tell the student that they are out of matches. If the software follows belligerence path 219, repetition step 220 will tell the student to try again later, or issue a similarly appropriate message. If the software cooperates with the student via cooperation path 221, as it most likely will, then the program returns to either the SMOKING ACTION module 203, BUMMING module 222, or INFORMATION ACTION module 223.

Figure 16:
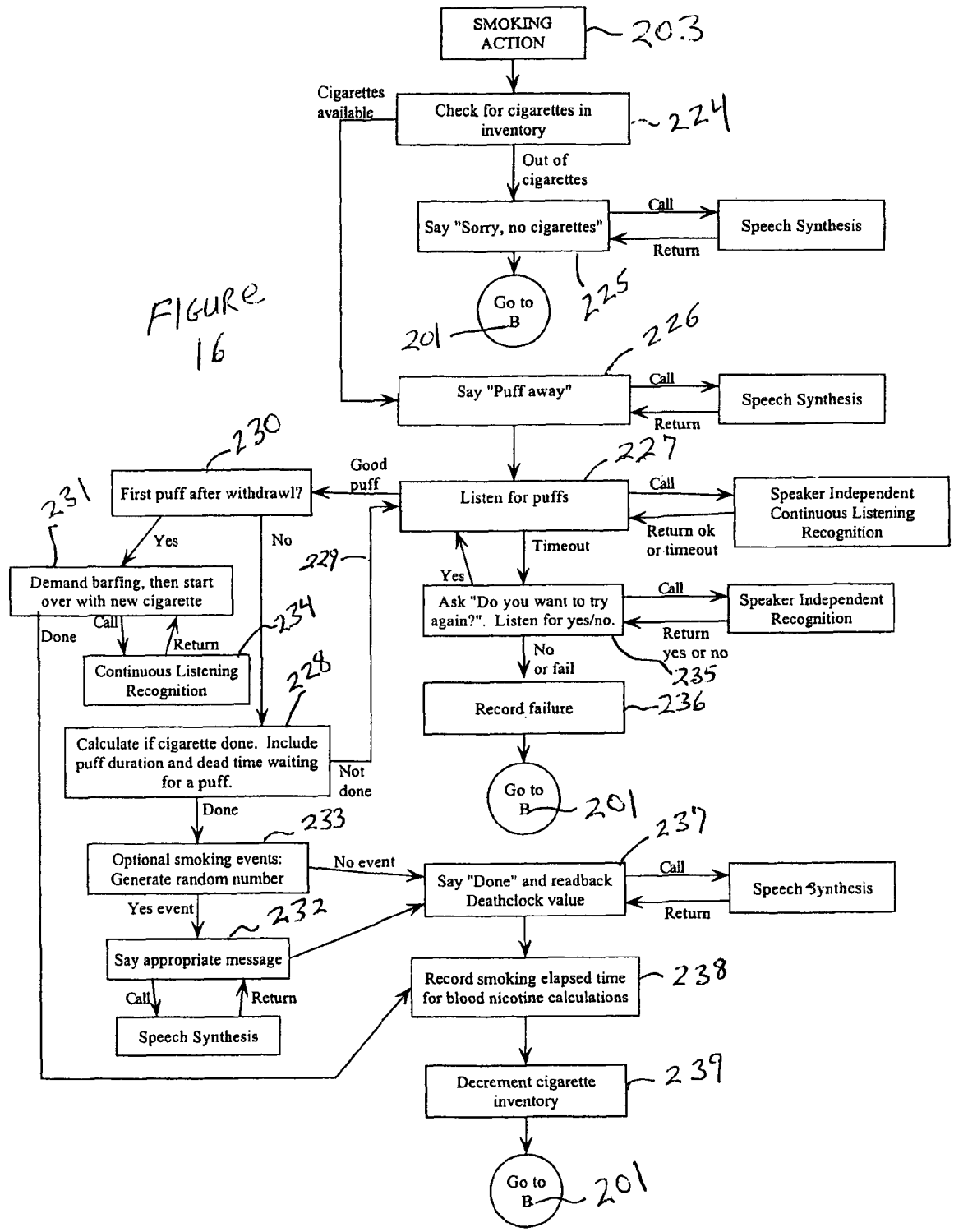
FIG. 16 is a flowchart depicting the SMOKING ACTION subroutine utilized with the present invention.

Referring also to FIG. 16, the SMOKING procedure 203 begins with an inventory inquiry 224 to see if there are any simulated cigarettes remaining in inventory. If not, the device 1 will so inform the student via announcement 225 and then return to the RUN module 171 for recalculations 201 and SLEEP 174. From the RUN module 171 the student can either wake the device and bum a cigarette from another student via module 222, or "buy" cigarettes from the teacher. If there are cigarettes remaining, the device will execute announcement 226 and tell the student to "Puff away," then enter a Continuous Listening subroutine 227 to listen for the generation of a satisfaction signal (i.e., puffs) at variable intervals.

When each puff is recognized, the consumption rate step 228 will calculate how much of the cigarette has been smoked. This calculation 228 will include the intensity and duration of the puff as well as the interval since the last puff.

If the cigarette is not done, the program will follow return path 229 to subroutine 227 and listen for another puff. If this was the first puff occurring after nicotine withdrawal as calculated by counter 230, the program will execute demand 231 for a retching sound from the student. After the retch is recognized the device 1 will tell the student, via message bank 232 a message chosen by random message generator 233 such as "You just barfed on your lit cigarette. You must smoke another, after washing your hands." or "Barf into a toilet, then flush the toilet." The device 1 will listen for and recognize via sound monitor 234 the sound of the toilet flushing. If no puff is heard at step 227, the software will continue to ask the student by interrogatory 235 if they wish to try again. If not, the software will record a failure 236 and return to the RUN module parameter calculator 201.

When the cigarette is done there may be another randomly generated message 233 such as the device 1 saying, for example, "You burned your fingers! Scream out loud!" or "You burned a nearby piece of furniture. Put a stickon burn decal on a nearby piece of furniture." After a pause, the device 1 enables deathclock monitor 237 and says "Done" and reads out the value of the Deathclock. The software records the accumulated duration and intensity of puffs from this cigarette at recorder 238 for use by the RUN module 171 in recalculating blood nicotine level at calculator 201. Then the cigarette inventory 239 is decremented, and the software returns to the RUN module 171 for recalculation 201 and SLEEP 174.

The software can allow a student to preemptively smoke a cigarette (i.e., simulate smoking of a cigarette before receiving a smoking demand) in order to delay generation of the next scheduled smoking notice. Such an option provides the student with limited control over the scheduled timing of smoking demands so as to permit an attentive student to adjust smoking demands to the students schedule. A variety of programming options are available for allowing preemptive smoking. Exemplary options include (i) restarting the current time interval between smoking demands when a preemptive smoke occurs within the last half of the current interval and (ii) increasing the current interval between smoking demands by one half of the scheduled interval (e.g., a 60 minute interval becomes a 90 minute interval) when a preemptive smoke occurs within the interval.

The device 1 can simulate the development of tolerance for nicotine by incrementally increasing the amount of simulated addictant which must be decremented from inventory in order to respond to an addictant demand signal. The incremental increase can be based upon a variety of factors, including the cumulative number of times addictant has been decremented from inventory throughout an assignment period or the cumulative amount of addictant decremented from inventory throughout an assignment period.

An alternative to the requirement that a student actually puff on a simulated cigarette 17 to generate a satisfaction signal, involves use of the sound monitor 234 to detect and recognize a student speaking a predetermined anti-smoking message (e.g., repeatedly stating "smoking is bad for your health") and programming of the software to generate the satisfaction signal upon detection of the required mantra.

Figure 17:
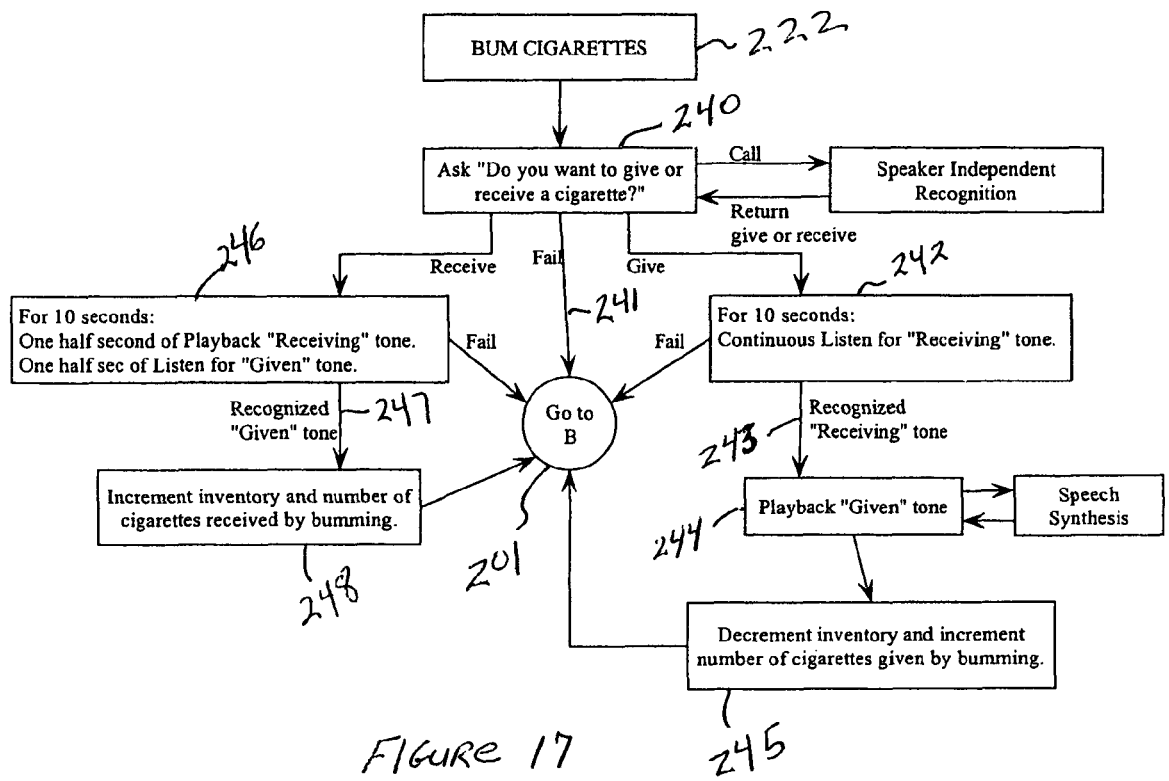
FIG. 17 is a flowchart depicting the BUM CIGARETTES subroutine which forms a part of the present invention.

Students must perceive this overall simulation device 1 as realistic in order to embrace and make the most of the educational experience. Borrowing or "bumming" cigarettes is a realistic feature of the device 1 intended to encourage active communication among students. As best understood by reference to FIG. 17, if two students with similar devices 1 agree that one will allow the other to bum a cigarette from him, then the two of them will simultaneously wakeup their devices 1 and command them to enable the BUM cigarettes module 222.

Each device 1 will ask its student whether they choose to give or receive a cigarette at question 240. The donating device 1 will check its inventory to ensure that it has cigarettes to give. If there are none, device 1 will inform the student along failure path 241 and return to RUN module 171 physiological parameter calculations step 201 and SLEEP mode 174. If the device 1 does have cigarettes to give, device 1 will listen 242 for a unique "Receiving" tone from the other device 1 asking for a cigarette. When the software recognizes 243 the "Receiving" tone device 1 will immediately playback 244 a unique "Given" tone (actually a secret composite tone so it is difficult to counterfeit) for a few seconds. Then the software will decrement 245 its inventory of cigarettes and return to the RUN module 171 physiological parameter calculations step 201 and SLEEP mode 174.

The "Receiving" device 1 will begin a loop 246, lasting a maximum of ten seconds, during which loop 246 will alternately playback the "Receiving" tone for half a second, then listen for half a second for the "Given" tone of acknowledgement from the other device 1. Once device 1 recognizes 247 the "Given" tone, the software increments 248 its inventory and returns to the RUN module 171 physiological parameter to calculations step 201 and SLEEP 174.

The total number of cigarettes given and received is recorded and reported to the teacher so that cheating (e.g., bumming one cigarette to multiple receivers simultaneously, or tape recording the "Given" tone) can be easily detected. One can eliminate cheating by embedding a unique two-way code in the transmitted tones, or by requiring one-to-one physical connection between devices for communications. Typically, the device's added complexity and cost are not warranted since occasional counting by the teacher will suffice to deter cheating.

There are many methods of communicating between devices for bumming cigarettes. As a passive example, one might install contacts on each box connected to a 100K ohm resistor. When the devices are touched together in parallel, the resistance drops to 50K ohm. The microcontroller 19 can measure this resistance reduction. As an active example, the students might touch together contacts on the devices while pushing appropriate buttons. The preferred approach adds no hardware or software beyond that which already exists for tone playback and recognition.

In order to provide a realistic simulation of addictive behavior, the device 1 should be able to differentiate between the waking hours ("daily schedule") and sleeping hours ("bedtime schedule") of a student, as the behavior of a smoker is substantially different during these two periods. Rather than force a student to alter his/her schedule to conform to a preconceived notion of a "normal" bedtime schedule, a BEDTIME module 260 can be provided. To initiate a bedtime period, the student presses the Student Pushbutton 163 and selects the bedtime option. Upon activation of the BEDTIME module 260, a bedtime schedule is entered wherein the scheduling of smoking, coughing and information interrupts is significantly decreased, often to zero during the initial portion of the assignment period.

The duration of the bedtime period can be of fixed or bounded random duration. When of fixed duration, the bedtime period can be between about 5 to 10 hours, preferably between about 6 to 9, with a preference for a duration of about 7½ to 8½ hours. When of bounded random duration, the bedtime period is randomly selected to fall between the predetermined boundaries of about 5 to 10 hours, preferably between about 6 to 9, with a preference for about 7½ to 8½ hours.

Upon completion of the bedtime period, the software returns to a daily schedule wherein the scheduling of smoking, coughing and information interrupts is increased to reflect the behavior of a smoker during waking hours.

In order to prevent a student from continuously entering the BEDTIME module 260, the software can be programmed to require a minimum daily schedule period between sequential bedtime periods. The duration of the minimum daily schedule period can be of fixed or bounded random duration. When of fixed duration, the minimum daily schedule period, measured from initiation to initiation of sequential bedtime periods, can be selected from between about 12 to 20 hours, preferably selected from between about 14 to 18 hours, with a preference for between about 14 to 16 hours. When of bounded random duration, the minimum daily schedule period is randomly selected to fall between the predetermined boundaries between about 12 to 20 hours, preferably between about 14 to 18 hours, with a preference for between about 14 to 16 hours.

Figure 18:
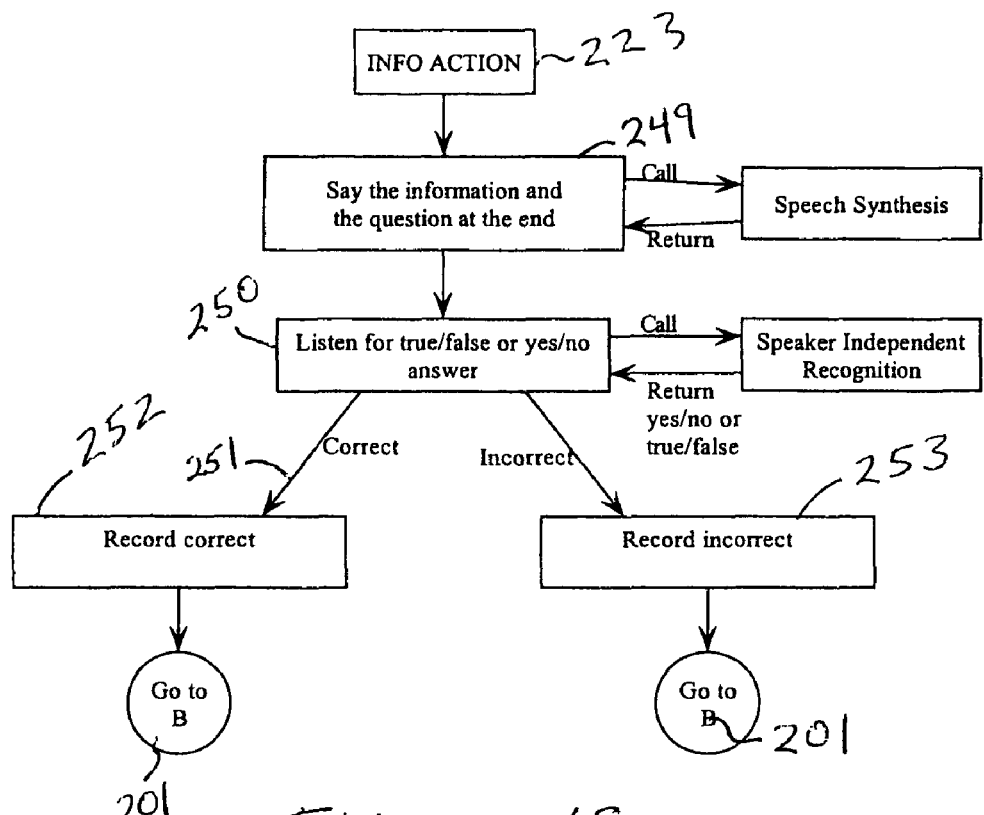
FIG. 18 is a flowchart depicting the INFO ACTION subroutine utilized during operation of the present invention.

As best seen in FIG. 18, every piece of educational information that is recited by the device 1 ends with a true/false or yes/no question 249. Listening interval 250 begins thereafter to determine if the student has answered the question 249. The student must give the correct answer 251 to the question 249 in order to prevent the information from being repeated at some later time. The software records whether the question was answered correctly at register 252 or incorrectly at register 253 before returning to the RUN module 171 for recalculation 201 and SLEEP mode 174.

As those skilled in the art will appreciate, the simulator 1 can be equipped with a variety of different programs with different timings, information, and curriculum depending on the particular addictant to be simulated by the device 1, for example, smoking tobacco, smoking marijuana, ingesting cocaine, or injecting other drugs.

The simulator 1 can also be equipped with a variety of modules patterned after the COUGHING INTERRUPT module 211 wherein the simulation of any of a variety of different voluntary and/or involuntary addiction-induced actions are demanded and detected, such as vomiting, payment of money, unscheduled travel to purchase cigarettes, etc.

I claim:

1. An addiction simulator for use in an educational program for simulating addictive behavior effected by addiction to an addictant without means for dispensing of the addictant, comprising:
   (a) an enclosure; and
   (b) an addictive behavior simulation system within the enclosure for periodically requesting simulated addictive behavior, including at least:
      (i) a means for generating a perceptible addictant demand signal;
      (ii) an interval timer in communication with the addictant demand signal generating means for initiating generation of the addictant demand signal at intervals selected from (A) intervals of substantially identical duration, (B) intervals of varying and patternless duration, and (C) intervals of diminishing duration representative of the development of tolerance for the requested addictant; and
      (iii) an inventory control system comprising an electronic circuit effective for:
         (A) generating an initial addictant inventory value;
         (B) detecting a request for addictant from an assigned individual in response to a generated addictant demand signal, including detection of the amount of addictant requested;
         (C) decrementing the addictant inventory value in response to a detected request for addictant by the amount of addictant requested when the inventory value is greater than the amount of addictant requested; and
         (D) generating a perceptible refusal signal in response to a detected request for addictant when the addictant inventory value is less than the amount of addictant requested.

2. An addiction simulator for use in an educational program for simulating addictive behavior effected by addiction to an addictant without means for dispensing of the addictant, comprising:
   (a) an enclosure; and
   (b) an addictive behavior simulation system within the enclosure for periodically requesting simulated addictive behavior, including at least:
      (i) a means for periodically generating a continuous or repetitive perceptible addictant demand signal;
      (ii) a means for receiving a satisfaction signal from an assigned individual in response to a generated perceptible addictant demand signal;
      (iii) a means in communication with the addictant demand signal generating means and the satisfaction signal receiving means for terminating continued or repetitive generation of the perceptible addictant demand signal upon receipt of the satisfaction signal, and
      (iv) an inventory control system comprising an electronic circuit effective for:
         (A) generating an initial addictant inventory value;
         (B) detecting a request for addictant from an assigned individual in response to a generated addictant demand signal, including detection of the amount of addictant requested;
         (C) decrementing the addictant inventory value in response to a detected request for addictant by the amount of addictant requested when the inventory value is greater than the amount of addictant requested; and
         (D) generating a perceptible refusal signal in response to a detected request for addictant when the addictant inventory value is less than the amount of addictant requested.

3. An addiction simulator for use in an educational program for simulating addictive behavior effected by addiction to an addictant without means for dispensing of the addictant, comprising:
   (a) an enclosure; and
   (b) an addictive behavior simulation system within the enclosure for periodically requesting simulated addictive behavior, including at least:
      (i) a means for periodically generating a continuous or repetitive perceptible addictant demand signal;
      (ii) a means for receiving a satisfaction signal from an assigned individual in response to a generated perceptible addictant demand signal;
      (iii) a means in communication with the addictant demand signal generating means and the satisfaction signal receiving means for terminating continued or repetitive generation of the perceptible addictant demand signal upon receipt of the satisfaction signal, and (iv) an interval timer in communication with the addictant demand signal generating means for initiating generation of the addictant demand signal at intervals, wherein the duration of the interval between the generation of sequential addictant demand signals is a function of at least the values of a simulated blood addictant content determined for an assigned individual, wherein the value of the simulated blood addictant content is determined at least in part by:

(A) gathering at least one physiological addictant response data point of the assigned individual;

(B) measuring passage of time since a simulated intake of addictant by the assigned individual; and (C) periodically determining the value of the simulated blood addictant content for the assigned individual as a function of at least the measured passage of time since the simulated intake of addictant and the physiological addictant response data point gathered for the assigned individual.

4. The addiction simulator of claim 2 further comprising a means in communication with the addictant demand signal generating means and the satisfaction signal receiving means for recording data indicative of the time interval between generation of the addictant demand signal and receipt of the satisfaction signal for subsequent review.

5. The addiction simulator of claim 3 further comprising a means in communication with the addictant demand signal generating means and the satisfaction signal receiving means for recording data indicative of the time interval between generation of the addictant demand signal and receipt of the satisfaction signal for subsequent review.

6. The addiction simulator of claim 1 wherein the addictive behavior simulation system further comprises:

(a) a means for generating a perceptible message indicating the occurrence of an involuntary addiction-induced physical action; and (b) an interval timer in communication with the perceptible involuntary action indication generating means for initiating generation of the message at intervals selected from (A) intervals of substantially identical duration, (B) intervals of varying and patternless duration, and (C) intervals of diminishing duration representative of the onset and development of involuntary addiction-induced physical side-effects.

7. The addiction simulator of claim 2 wherein the addictive behavior simulation system further comprises:

(a) a means for generating a perceptible message indicating the occurrence of an involuntary addiction-induced physical action; and (b) an interval timer in communication with the perceptible involuntary action indication generating means for initiating generation of the message at intervals selected from (A) intervals of substantially identical duration, (B) intervals of varying and patternless duration, and (C) intervals of diminishing duration representative of the onset and development of involuntary addiction-induced physical side-effects.

8. The addiction simulator of claim 3 wherein the addictive behavior simulation system further comprises:

(a) a means for generating a perceptible message indicating the occurrence of an involuntary addiction-induced physical action; and (b) an interval timer in communication with the perceptible involuntary action indication generating means for initiating generation of the message at intervals selected from (A) intervals of substantially identical duration, (B) intervals of varying and patternless duration, and (C) intervals of diminishing duration representative of the onset and development of involuntary addiction-induced physical side-effects.

9. The addiction simulator of claim 6 wherein the perceptible involuntary action indicating means includes a speaker for creating an audible message indicating at least one action selected from coughing and vomiting.

10. The addiction simulator of claim 7 wherein the perceptible involuntary action indicating means includes a speaker for creating an audible message indicating at least one action selected from coughing and vomiting.

11. The addiction simulator of claim 8 wherein the perceptible involuntary action indicating means includes a speaker for creating an audible message indicating at least one action selected from coughing and vomiting.

12. The addiction simulator of claim 6 wherein the perceptible involuntary action message indicating means includes an alphanumeric display for generating a visible message indicating the occurrence of an involuntary addiction-induced physical action.

13. The addiction simulator of claim 7 wherein the perceptible involuntary action message indicating means includes an alphanumeric display for generating a visible message indicating the occurrence of an involuntary addiction-induced physical action.

14. The addiction simulator of claim 8 wherein the perceptible involuntary action message indicating means includes an alphanumeric display for generating a visible message indicating the occurrence of an involuntary addiction-induced physical action.

15. The addiction simulator of claim 12 wherein the alphanumeric display is effective for creating a visual representation of at least one action selected from coughing and vomiting.

16. The addiction simulator of claim 13 wherein the alphanumeric display is effective for creating a visual representation of at least one action selected from coughing and vomiting.

17. The addiction simulator of claim 14 wherein the alphanumeric display is effective for creating a visual representation of at least one action selected from coughing and vomiting.

18. The addiction simulator of claim 1 wherein the addictive behavior simulation system further comprises:

(a) a means for generating a perceptible message demanding that an assigned individual simulate an involuntary addiction-induced physical action; and (b) an interval timer in communication with the perceptible involuntary action demand generating means for initiating generation of the message at intervals selected from (A) intervals of substantially identical duration, (B) intervals of varying and patternless duration, and (C) intervals of diminishing duration representative of the onset and development of involuntary addiction-induced physical side-effects.

19. The addiction simulator of claim 2 wherein the addictive behavior simulation system further comprises:

(a) a means for generating a perceptible message demanding that an assigned individual simulate an involuntary addiction-induced physical action; and (b) an interval timer in communication with the perceptible involuntary action demand generating means for initiating generation of the message at intervals selected from (A) intervals of substantially identical duration, (B)

intervals of varying and patternless duration, and (C) intervals of diminishing duration representative of the onset and development of involuntary addiction-induced physical side-effects.

20. The addiction simulator of claim 3 wherein the addictive behavior simulation system further comprises:
   (a) a means for generating a perceptible message demanding that an assigned individual simulate an involuntary addiction-induced physical action; and
   (b) an interval timer in communication with the perceptible involuntary action demand generating means for initiating generation of the message at intervals selected from (A) intervals of substantially identical duration, (B) intervals of varying and patternless duration, and (C) intervals of diminishing duration representative of the onset and development of involuntary addiction-induced physical side-effects.

21. The addiction simulator of claim 18 wherein the perceptible involuntary action demanding means includes a speaker for creating an audible demand message selected from a command to simulate coughing and a command to simulate vomiting.

22. The addiction simulator of claim 19 wherein the perceptible involuntary action demanding means includes a speaker for creating an audible demand message selected from a command to simulate coughing and a command to simulate vomiting.

23. The addiction simulator of claim 20 wherein the perceptible involuntary action demanding means includes a speaker for creating an audible demand message selected from a command to simulate coughing and a command to simulate vomiting.

24. The addiction simulator of claim 18 wherein the perceptible involuntary action demanding means includes an alphanumeric display for generating a visible message directing the assigned individual to simulate an involuntary addiction-induced physical action.

25. The addiction simulator of claim 19 wherein the perceptible involuntary action demanding means includes an alphanumeric display for generating a visible message directing the assigned individual to simulate an involuntary addiction-induced physical action.

26. The addiction simulator of claim 20 wherein the perceptible involuntary action demanding means includes an alphanumeric display for generating a visible message directing the assigned individual to simulate an involuntary addiction-induced physical action.

27. The addiction simulator of claim 24 wherein the alphanumeric display is effective for creating a visual representation of at least one action selected from coughing and vomiting.

28. The addiction simulator of claim 25 wherein the alphanumeric display is effective for creating a visual representation of at least one action selected from coughing and vomiting.

29. The addiction simulator of claim 26 wherein the alphanumeric display is effective for creating a visual representation of at least one action selected from coughing and vomiting.

30. The addiction simulator of claim 18 wherein the addictive behavior simulation system further comprises a means for receiving an involuntary action completion signal from an assigned individual in response to generation of a perceptible message demanding simulation of an involuntary addiction-induced physical action and either (A) recording receipt of the involuntary action completion signal for subsequent review or (B) terminating continued or repetitive generation of the perceptible involuntary action demand message.

31. The addiction simulator of claim 19 wherein the addictive behavior simulation system further comprises a means for receiving an involuntary action completion signal from an assigned individual in response to generation of a perceptible message demanding simulation of an involuntary addiction-induced physical action and either (A) recording receipt of the involuntary action completion signal for subsequent review or (B) terminating continued or repetitive generation of the perceptible involuntary action demand message.

32. The addiction simulator of claim 20 wherein the addictive behavior simulation system further comprises a means for receiving an involuntary action completion signal from an assigned individual in response to generation of a perceptible message demanding simulation of an involuntary addiction-induced physical action and either (A) recording receipt of the involuntary action completion signal for subsequent review or (B) terminating continued or repetitive generation of the perceptible involuntary action demand message.

33. The addiction simulator of claim 30 wherein the involuntary action completion signal is a signal generated by actual audible performance of the demanded involuntary addiction-induced action.

34. The addiction simulator of claim 31 wherein the involuntary action completion signal is a signal generated by actual audible performance of the demanded involuntary addiction-induced action.

35. The addiction simulator of claim 32 wherein the involuntary action completion signal is a signal generated by actual audible performance of the demanded involuntary addiction-induced action.

36. The addiction simulator of claim 30 wherein the demanded involuntary action is selected from coughing and vomiting.

37. The addiction simulator of claim 31 wherein the demanded involuntary action is selected from coughing and vomiting.

38. The addiction simulator of claim 32 wherein the demanded involuntary action is selected from coughing and vomiting.

39. The addiction simulator of claim 1 wherein the addictive behavior simulation system further comprises:
   (a) a means for generating a perceptible message indicating the occurrence of a voluntary addiction-induced action; and
   (b) an interval timer in communication with the voluntary action indication generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

40. The addiction simulator of claim 2 wherein the addictive behavior simulation system further comprises:
   (a) a means for generating a perceptible message indicating the occurrence of a voluntary addiction-induced action; and
   (b) an interval timer in communication with the voluntary action indication generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

41. The addiction simulator of claim 3 wherein the addictive behavior simulation system further comprises:
   (a) a means for generating a perceptible message indicating the occurrence of a voluntary addiction-induced action; and
   (b) an interval timer in communication with the voluntary action indication generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

42. The addiction simulator of claim 39 wherein the perceptible voluntary action indicating means includes a speaker for creating an audible message representing the payment of money.

43. The addiction simulator of claim 40 wherein the perceptible voluntary action indicating means includes a speaker for creating an audible message representing the payment of money.

44. The addiction simulator of claim 41 wherein the perceptible voluntary action indicating means includes a speaker for creating an audible message representing the payment of money.

45. The addiction simulator of claim 39 wherein the voluntary action indicating means includes an alphanumeric display for generating a visible message representing the payment of money.

46. The addiction simulator of claim 40 wherein the voluntary action indicating means includes an alphanumeric display for generating a visible message representing the payment of money.

47. The addiction simulator of claim 41 wherein the voluntary action indicating means includes an alphanumeric display for generating a visible message representing the payment of money.

48. The addiction simulator of claim 1 wherein the addictive behavior simulation system further comprises:
   (a) a means for generating a message demanding that an assigned individual simulate a voluntary addiction-induced action; and
   (b) an interval timer in communication with the voluntary action demand generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

49. The addiction simulator of claim 2 wherein the addictive behavior simulation system further comprises:
   (a) a means for generating a message demanding that an assigned individual simulate a voluntary addiction-induced action; and
   (b) an interval timer in communication with the voluntary action demand generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

50. The addiction simulator of claim 1 wherein the addictive behavior simulation system further comprises:
   (a) a means for generating a message demanding that an assigned individual simulate a voluntary addiction-induced action; and
   (b) an interval timer in communication with the voluntary action demand generating means for initiating generation of the message at intervals selected from (A) intervals of substantially identical duration, (B) intervals of varying and patternless duration, and (C) intervals of diminishing duration representative of an increase in voluntary activity devoted to the simulated addiction due to the simulated development of a tolerance for the addictant.

51. The addiction simulator of claim 48 wherein the voluntary action demanding means includes a speaker for creating an audible demand to pay money.

52. The addiction simulator of claim 49 wherein the voluntary action demanding means includes a speaker for creating an audible demand to pay money.

53. The addiction simulator of claim 50 wherein the voluntary action demanding means includes a speaker for creating an audible demand to pay money.

54. The addiction simulator of claim 48 wherein the voluntary action demanding means includes an alphanumeric display for generating a visible demand to pay money.

55. The addiction simulator of claim 49 wherein the voluntary action demanding means includes an alphanumeric display for generating a visible demand to pay money.

56. The addiction simulator of claim 50 wherein the voluntary action demanding means includes an alphanumeric display for generating a visible demand to pay money.

57. The addiction simulator of claim 48 wherein the addictive behavior simulation system further comprises a means for receiving a voluntary action completion signal from an assigned individual in response to generation of a message demanding simulation of a voluntary action signal and either (A) recording receipt of the voluntary action completion signal for subsequent review or (B) terminating continued or repetitive generation of the involuntary action demand message.

58. The addiction simulator of claim 49 wherein the addictive behavior simulation system further comprises a means for receiving a voluntary action completion signal from an assigned individual in response to generation of a message demanding simulation of a voluntary action signal and either (A) recording receipt of the voluntary action completion signal for subsequent review or (B) terminating continued or repetitive generation of the involuntary action demand message.

59. The addiction simulator of claim 50 wherein the addictive behavior simulation system further comprises a means for receiving a voluntary action completion signal from an assigned individual in response to generation of a message demanding simulation of a voluntary action signal and either (A) recording receipt of the voluntary action completion signal for subsequent review or (B) terminating continued or repetitive generation of the involuntary action demand message.

60. The addiction simulator of claim 57 wherein the voluntary action completion signal is a signal generated by actual simulated performance of the demanded voluntary addiction-induced action.

61. The addiction simulator of claim 58 wherein the voluntary action completion signal is a signal generated by actual simulated performance of the demanded voluntary addiction-induced action.

62. The addiction simulator of claim 59 wherein the voluntary action completion signal is a signal generated by actual simulated performance of the demanded voluntary addiction-induced action.

63. The addiction simulator of claim 60 wherein the demanded voluntary action is the payment of money and the means for receiving the voluntary action completion signal includes (A) a slot through the enclosure configured and arranged to permit the introduction of an object representative of money and (B) a momentary contact switch mounted adjacent the slot so as to sense the introduction of the object into the slot and generate the voluntary action completion signal upon sensing of the object by the momentary contact switch.

64. The addiction simulator of claim 61 wherein the demanded voluntary action is the payment of money and the means for receiving the voluntary action completion signal includes (A) a slot through the enclosure configured and arranged to permit the introduction of an object representative of money and (B) a momentary contact switch mounted adjacent the slot so as to sense the introduction of the object into the slot and generate the voluntary action completion signal upon sensing of the object by the momentary contact switch.

65. The addiction simulator of claim 62 wherein the demanded voluntary action is the payment of money and the means for receiving the voluntary action completion signal includes (A) a slot through the enclosure configured and arranged to permit the introduction of an object representative of money and (B) a momentary contact switch mounted adjacent the slot so as to sense the introduction of the object into the slot and generate the voluntary action completion signal upon sensing of the object by the momentary contact switch.

66. The addiction simulator of claim 2 further comprising an interval timer in communication with the addictant demand signal generating means for initiating generation of the addictant demand signal at intervals, wherein the duration of the interval between the generation of sequential addictant demand signals is a function of at least the presence or absence of the receipt of an satisfaction signal in response to a previous addictant demand signal.

67. The addiction simulator of claim 3 further comprising an interval timer in communication with the addictant demand signal generating means for initiating generation of the addictant demand signal at intervals, wherein the duration of the interval between the generation of sequential addictant demand signals is a function of at least the presence or absence of the receipt of an satisfaction signal in response to a previous addictant demand signal.

68. The addiction simulator of claim 3 wherein (i) the simulated blood addictant content for the assigned individual is periodically calculated as a function of at least the measured passage of time since the simulated intake of addictant and the physiological addictant response data point gathered for the assigned individual, and (ii) the perceptible addictant demand signal is generated when the calculated simulated blood addictant content falls below a defined minimum threshold value.

69. The addiction simulator of claim 3 further comprising: (D) generating a perceptible withdrawal signal when the simulated addictant blood level falls an additional defined amount below the defined minimum threshold value.

70. The addiction simulator of claim 3 further comprising: (E) detecting the simulated intake of addictant by the assigned individual, and then (F) repeating (B) and (C) based upon timing of the simulated intake of addictant at (E).

71. The addiction simulator of claim 69 further comprising: (E) detecting the simulated intake of addictant by the assigned individual, and then (F) repeating (B) and (C) based upon timing of the simulated intake of addictant at (E).

72. The addiction simulator of claim 3 wherein the minimum threshold value is incrementally increased as a function of the number of times the simulated intake of addictant is detected, representative of the development of tolerance for the addictant.

73. The addiction simulator of claim 3 wherein the value of the simulated addictant blood level concentration is further a function of the simulated amount of addictant indicated as having been taken by the assigned individual.

74. The addiction simulator of claim 2 wherein the satisfaction signal is a signal generated by actual simulated performance of the introduction of the requested addictant into the body of the assigned individual.

75. The addiction simulator of claim 3 wherein the satisfaction signal is a signal generated by actual simulated performance of the introduction of the requested addictant into the body of the assigned individual.

76. The addiction simulator of claim 2 wherein the satisfaction signal is a signal generated by actual performance of a predetermined anti-addictant activity.

77. The addiction simulator of claim 3 wherein the satisfaction signal is a signal generated by actual performance of a predetermined anti-addictant activity.

78. The addiction simulator of claim 1 wherein the addictant is nicotine.

79. The addiction simulator of claim 2 wherein the addictant is nicotine.

80. The addiction simulator of claim 3 wherein the addictant is nicotine.

81. The addiction simulator of claim 78 wherein the enclosure has the approximate size and shape of a cigarette package.

82. The addiction simulator of claim 79 wherein the enclosure has the approximate size and shape of a cigarette package.

83. The addiction simulator of claim 80 wherein the enclosure has the approximate size and shape of a cigarette package.

84. The addiction simulator of claim 1 wherein the means for generating an addictant demand signal includes a speaker for generating an audible addictant demand signal.

85. The addiction simulator of claim 2 wherein the means for generating an addictant demand signal includes a speaker for generating an audible addictant demand signal.

86. The addiction simulator of claim 3 wherein the means for generating an addictant demand signal includes a speaker for generating an audible addictant demand signal.

87. The addiction simulator of claim 1 wherein the means for generating an addictant demand signal includes a vibrator for generating a tactile addictant demand signal.

88. The addiction simulator of claim 2 wherein the means for generating an addictant demand signal includes a vibrator for generating a tactile addictant demand signal.

89. The addiction simulator of claim 3 wherein the means for generating an addictant demand signal includes a vibrator for generating a tactile addictant demand signal.

90. The addiction simulator of claim 1 wherein the means for generating an addictant demand signal includes an alphanumeric display for generating a visible addictant demand signal.

91. The addiction simulator of claim 2 wherein the means for generating an addictant demand signal includes an alphanumeric display for generating a visible addictant demand signal.

92. The addiction simulator of claim 3 wherein the means for generating an addictant demand signal includes an alphanumeric display for generating a visible addictant demand signal.

93. The addiction simulator of claim 2 wherein element (b)(iii) is a means for terminating continued or repetitive generation of the perceptible addictant demand signal upon receipt of the satisfaction signal, and the terminating means is an electronic circuit.

94. The addiction simulator of claim 3 wherein element (b)(iii) is a means for terminating continued or repetitive generation of the perceptible addictant demand signal upon receipt of the satisfaction signal, and the terminating means is an electronic circuit.

95. The addiction simulator of claim 74 wherein the addictant is nicotine and the activity simulating introduction of the requested addictant into the body is selected from (i) inhaling or exhaling air through a breathing tube, and (ii) placing a simulated cigarette between the lips of the assigned individual.

96. The addiction simulator of claim 75 wherein the addictant is nicotine and the activity simulating introduction of the requested addictant into the body is selected from (i) inhaling or exhaling air through a breathing tube, and (ii) placing a simulated cigarette between the lips of the assigned individual.

97. The addiction simulator of claim 76 wherein the addictant is nicotine and the anti-addictant activity is speaking an anti-smoking message.

98. The addiction simulator of claim 77 wherein the addictant is nicotine and the anti-addictant activity is speaking an anti-smoking message.

\* \* \* \* \*